US010563250B2

(12) United States Patent
Liu et al.

(10) Patent No.: US 10,563,250 B2
(45) Date of Patent: Feb. 18, 2020

(54) METHODS, COMPOSITIONS AND KITS FOR SMALL RNA CAPTURE, DETECTION AND QUANTIFICATION

(71) Applicant: LIFE TECHNOLOGIES CORPORATION, Carlsbad, CA (US)

(72) Inventors: Chunmei Liu, Palo Alto, CA (US); Shoulian Dong, Mountain View, CA (US); Linda Wong, San Bruno, CA (US)

(73) Assignee: Life Technologies Corporation, Carlsbad, CA (US)

( * ) Notice: Subject to any disclaimer, the term of this patent is extended or adjusted under 35 U.S.C. 154(b) by 452 days.

(21) Appl. No.: 15/066,139

(22) Filed: Mar. 10, 2016

(65) Prior Publication Data
US 2016/0265031 A1 Sep. 15, 2016

Related U.S. Application Data

(60) Provisional application No. 62/133,185, filed on Mar. 13, 2015.

(51) Int. Cl.
C12P 19/34 (2006.01)
C12Q 1/686 (2018.01)

(52) U.S. Cl.
CPC .................... C12Q 1/686 (2013.01)

(58) Field of Classification Search
CPC ........ C12Q 2525/207; C12Q 2521/501; C12Q 2525/173; C12Q 2525/191; C12Q 1/6806; C12Q 1/6809; C12Q 1/6851; C12Q 2525/155; C12Q 2561/125; C12Q 2565/519; C12Q 1/686
USPC ....................................... 425/91.2
See application file for complete search history.

(56) References Cited

U.S. PATENT DOCUMENTS

| | | | |
|---|---|---|---|
| 5,770,365 A | 6/1998 | Lane et al. | |
| 6,706,476 B1* | 3/2004 | Thirstrup | C07H 21/04 435/6.12 |
| 7,361,465 B2 | 4/2008 | Murphy et al. | |
| 8,192,937 B2 | 6/2012 | Jacobsen et al. | |
| 8,383,344 B2 | 2/2013 | Jacobsen et al. | |
| 8,575,071 B2 | 11/2013 | Lau et al. | |
| 8,741,569 B2 | 6/2014 | Lao et al. | |
| 8,809,022 B2 | 8/2014 | Tuschl et al. | |
| 8,927,245 B2 | 1/2015 | Zeiner et al. | |
| 8,940,487 B2 | 1/2015 | Spier | |
| 9,012,149 B2 | 4/2015 | Kim et al. | |
| 9,096,895 B2 | 8/2015 | Busk et al. | |
| 9,115,389 B2 | 8/2015 | Gilad et al. | |
| 9,169,507 B2 | 10/2015 | Tuschl et al. | |
| 9,217,173 B2 | 12/2015 | Engel et al. | |
| 9,249,459 B2 | 2/2016 | Hamilton et al. | |
| 9,290,801 B2 | 3/2016 | Wu et al. | |
| 9,416,405 B2 | 8/2016 | Dong et al. | |
| 2005/0272075 A1* | 12/2005 | Jacobsen | C12Q 1/6809 435/6.18 |
| 2007/0020672 A1 | 1/2007 | Wittwer et al. | |
| 2007/0031857 A1 | 2/2007 | Makarov et al. | |
| 2007/0054287 A1 | 3/2007 | Bloch | |
| 2007/0059752 A1 | 3/2007 | Cook | |
| 2007/0072208 A1 | 3/2007 | Drmanac | |
| 2007/0111226 A1 | 5/2007 | Tan et al. | |
| 2007/0117112 A1 | 5/2007 | Diener et al. | |
| 2008/0160529 A1 | 7/2008 | Brow et al. | |
| 2008/0194416 A1 | 8/2008 | Chen | |
| 2008/0248469 A1 | 10/2008 | Spier | |
| 2009/0061424 A1* | 3/2009 | Chen | C12Q 1/6809 435/6.12 |
| 2010/0279305 A1 | 11/2010 | Kuersten | |
| 2012/0015823 A1 | 1/2012 | Bignell et al. | |
| 2013/0045885 A1 | 2/2013 | Mohapatra et al. | |
| 2014/0128291 A1 | 5/2014 | Gu et al. | |
| 2014/0134614 A1 | 5/2014 | Dong et al. | |
| 2015/0105275 A1* | 4/2015 | Wong | C12Q 1/686 506/9 |
| 2017/0130264 A1 | 5/2017 | Dong et al. | |
| 2018/0171400 A1 | 6/2018 | Wong et al. | |

FOREIGN PATENT DOCUMENTS

| | | |
|---|---|---|
| CN | 100580089 C | 1/2010 |
| EP | 1735459 | 1/2012 |
| EP | 2052086 | 3/2013 |
| EP | 2391736 | 4/2015 |
| EP | 2914741 B1 | 8/2017 |
| EP | 3260558 A1 | 12/2017 |
| EP | 3268491 A1 | 1/2018 |

(Continued)

OTHER PUBLICATIONS

"TaqMan Advanced mi RNA Assays", Retrieved from the Internet: URL:https://tools.thermofisher.com/content/sfs/manuals/100027897_TaqManAdv_miRNA_Assays_UG.pdf, Jun. 5, 2015, 1-28.

Fu, H et al., "Identification of human fetal liver miRNAs by a novel method", Federation of European Biochemical Societies Letters, 579, Jun. 14, 2005, 3849-3854.

Hafner, M et al., "RNA-ligase-dependent biases in miRNA representation in deep-sequenced small RNA cDNA libraries", RNA, vol. 17, No. 9 Downloaded from rnajournal.cshlp.org on Jul. 16, 2014—Published by Cold Sgring Harbor Laboratory Press, Jul. 20, 2011, 1697-1712.

Nichols, N et al., "RNA Ligases", Current Protocols in Molecular Biology 3.15.1-3.15.4, Supplement 84, Oct. 2008, 2-5.

PCT/US2016/021679, "International Search Report", dated May 24, 2016, 5 pages.

(Continued)

Primary Examiner — Cynthia B Wilder

(57) ABSTRACT

Methods, compositions and kits for capturing, detecting and quantifying mature small RNAs are provided herein. Embodiments of the methods comprise tailing both the 5' and 3' ends of mature small RNA by ligating a 5' ligation adaptor to the 5' end and polyadenylating the 3' end. Other embodiments comprise reverse transcribing the adaptor ligated, polyadenylated mature small RNA with a universal reverse transcription primer and amplifying the cDNA with universal primers.

5 Claims, 12 Drawing Sheets

(56) References Cited

FOREIGN PATENT DOCUMENTS

| EP | 2914743 B1 | 8/2019 |
|---|---|---|
| WO | WO-2004013354 A1 | 2/2004 |
| WO | WO-2006084201 | 8/2006 |
| WO | WO-2007127999 A2 | 11/2007 |
| WO | WO-2008045251 A2 | 4/2008 |
| WO | WO-2008097957 A2 | 8/2008 |
| WO | WO-2011100057 A2 | 8/2011 |
| WO | WO-2011146942 | 11/2011 |
| WO | WO-2012033687 | 3/2012 |
| WO | WO-2012112714 | 8/2012 |
| WO | WO-2014071315 | 5/2014 |
| WO | WO-2014071322 | 5/2014 |
| WO | WO-2016149021 A1 | 9/2016 |

OTHER PUBLICATIONS

Pease, J, "Small-RNA sequencing libraries with greatly reduced adaptor-dimer background", *Nature Methods,* Mar. 2011, 2 pages.

Sridhara, S et al., "RNA-RNA ligation: Methods, Prospects and Applications", *GERF Bulletin of Biosciences, Green Earth Research Foundation,* vol. 2, No. 2, Dec. 1, 2011, 32-35.

Zhang, Z et al., "High-efficiency RNA cloning enables accurate quantification of miRNA expression by deep sequencing", *Genome Biology,* 14:R109, 2013, 13 pages.

Blewett, N. et al., "A quantitative assay for measuring mRNA decapping by splinted ligation reverse transcription polymerase chain reaction: qSL-RT-PCR", RNA Journal, vol. 17, No. 3, Cold Spring Harbor Laboratory Press, Mar. 2011, 535-543.

Huang, Y. et al., "The discovery approaches and detection methods of microRNAs", Molecular Biology Reports, vol. 38, No. 6, Nov. 25, 2010, 4125-4135.

Li, D et al., "Study on High Resolution Melting and Applications of the Same", Biotechnology Bulletin, No. 7, Jan. 4, 2009, 8 pages.

Maroney, et al., "Direct detection of small RNAs using splinted ligation", Nature Protocols, vol. 3, No. 2, 2008, 279-287.

PCT/US2013/068335, "International Search Report and Written Opinion dated Jan. 23, 2014", 14 pages.

PCT/US2013/068350, "International Search Report", dated Feb. 24, 2014, 6 pages.

PCT/US2013/068350, "Written Opinion", dated Feb. 24, 2014, 8 pages.

PCT/US2016/021679, "International Preliminary Report on Patentability", dated Sep. 19, 2017, 11 pages.

PCT/US2016/021679, "Written Opinion", dated May 24, 2016, 10 pages.

EP17186097.6, Extended European Search Report dated Sep. 20, 2017, 8 pages.

PCT/US2013/068335, "International Preliminary Report on Patentability Chapter I", dated May 14, 2015, 11 pages.

PCT/US2013/068350, "International Preliminary Report on Patentability Chapter I", dated May 14, 2015, 10 pages.

\* cited by examiner

METHODS, COMPOSITIONS AND KITS FOR SMALL RNA CAPTURE, DETECTION AND QUANTIFICATION

CROSS-REFERENCE TO RELATED APPLICATIONS

This application claims the benefit under 35 U.S.C. § 119(e) of U.S. Provisional Patent Application No. 62/133,185, filed Mar. 13, 2015, which is hereby incorporated by reference in its entirety.

FIELD

The present teachings are in the field of molecular and cell biology, specifically in the field of detecting target polynucleotides such as small RNA species.

INTRODUCTION

Small, non-coding, regulatory RNA species, such as microRNA (miRNA), are an abundant class of regulatory elements that have been shown to impact all aspects of normal cellular processes in both plants and animals, including cell death, differentiation, and proliferation. miRNAs have also been implicated in a number of diseases including cancer, heart disease and neurological diseases, consequently, miRNAs are studied as diagnostic and prognostic biomarkers. Small RNAs, including miRNAs, are generated by specific enzyme complexes from much larger RNA precursors. In general, a mature miRNA is composed of a highly conserved core sequence of 20-30 nucleotides and typically has a 5'-terminal monophosphate and a 3'-terminal hydroxyl group. miRNAs generally induce gene silencing by binding to target sites within the 3'-UTR of a targeted mRNA. This interaction suppresses protein synthesis and/or initiates mRNA degradation.

Attempts to detect, quantify and analyze mature small RNAs, such as miRNAs, have been hindered by several factors including their small sizes and similarity between related yet distinct species. Closely related miRNA family members can differ by only one nucleotide, thus there is a need for high specificity and the ability to discriminate between single nucleotide mismatches.

Nucleic acid microarrays have been used to quantify mature small RNAs, but this method requires a high concentration of input target for efficient hybridization. The small size of mature small RNAs precludes their amplification by quantitative or reverse transcriptase polymerase chain reaction (PCR), although the larger precursors may be amplified by PCR. Methods have been developed to facilitate PCR amplification of mature small RNAs. For example, mature small RNAs have been lengthened by the addition of at least one oligonucleotide adaptor. A need still exists for a method of small RNA capture, detection and analysis that is improved over the prior art with respect to at least one of the following attributes: sensitivity, speed, efficiency and cost-effectiveness.

SUMMARY

Provided herein are methods, compositions and kits for the capture and detection of mature small RNAs. In certain embodiments, the present teachings provide a method for capturing, detecting and quantifying a mature small RNA, such as a microRNA (miRNA), from a sample by polyadenylating the 3' end of the RNA, ligating a single-stranded universal adaptor to the 5' end of the RNA, and reverse transcribing the adaptor-ligated, polyadenylated RNA with a universal reverse transcription (RT) primer. The resulting reverse transcribed product comprises the cDNA of the mature small RNA and ligated adaptor with the universal RT primer at the 5'end. This cDNA product may be captured and/or detected or, using the universal sequences added at both the 5' and 3' ends, the cDNA product may undergo universal pre-amplification and/or amplification using a single pair of universal forward and reverse primers. Following such amplification reactions, the amplicons based on the mature small RNA may captured and/or detected. In certain embodiments, the target mature small RNA is a miRNA.

In certain embodiments, provided herein is a method for detecting a mature small RNA, the method including: with a sample comprising a mature small RNA, polyadenylating the 3' end of the mature small RNA and ligating a single-stranded adaptor to the 5' end of the mature small RNA in the presence of single strand RNA ligase to form an RNA ligation product, where the adaptor comprises a universal forward primer portion; reverse transcribing the RNA ligation product using a reverse transcription (RT) primer to form a cDNA product of the RNA ligation product, where the RT primer comprises a poly(T) portion and a tail portion and the tail portion comprises a universal reverse primer portion; amplifying the cDNA product using a first forward and reverse primer pair to form an amplification product, wherein the first forward primer can hybridize to the universal forward primer portion or its complement, and the first reverse primer can hybridize to the universal reverse primer portion or its complement; and detecting the amplification product corresponding to the mature small RNA via quantitative real-time polymerase chain reaction (qPCR).

In certain embodiments, the teachings provide a method for detecting a mature small RNA, the method including: with a sample comprising a mature small RNA, polyadenylating the 3' end of the mature small RNA and ligating a single-stranded adaptor to the 5' end of the mature small RNA in the presence of single strand RNA ligase to form an RNA ligation product, where the adaptor comprises a universal forward primer portion; reverse transcribing the RNA ligation product using a reverse transcription (RT) primer to form a cDNA product of the RNA ligation product, where the RT primer comprises a poly(T) portion and a tail portion and the tail portion comprises a universal reverse primer portion; pre-amplifying the cDNA product using a first forward and reverse primer pair to form an amplification product, wherein the first forward primer can hybridize to the universal forward primer portion or its complement, and the first reverse primer can hybridize to the universal reverse primer portion or its complement; and detecting the amplification product corresponding to the mature small RNA via qPCR, where the qPCR comprises a second forward and reverse primer pair, where at least one of the second forward primer and the second reverse primer comprises a portion specific to the mature small RNA.

In certain embodiments, a blocking agent may be used. Detection of the target polynucleotides may be performed using amplification methods such as the polymerase chain reaction (PCR), such as quantitative real-time PCR, quantitative endpoint PCR, and standard PCR. In certain embodiments, the amplification methods comprise the use of activation by polyphosphorolysis (APP) reactions and polyphosphorolyzing agents.

In certain embodiments, provided herein are kits comprising a single-stranded adaptor comprising a 3' terminal —OH group and a universal forward primer portion; a reverse transcription (RT) primer, where the RT primer comprises a poly(T) portion and a tail portion that comprises a universal reverse primer portion; a single strand RNA ligase, and a reverse transcriptase. In certain embodiments, the reverse transcriptase is a hot-start reverse transcriptase. In certain embodiments, the kit further comprises a DNA polymerase and a universal forward and reverse primer pair, where the universal forward primer can hybridize to the universal forward primer portion or its complement, and the universal reverse primer can hybridize to the universal reverse primer portion or its complement.

In certain embodiments, compositions, such as reaction compositions, are provided that comprise a single-stranded adaptor comprising a 3' terminal —OH group and a universal forward primer portion, a reverse transcription (RT) primer, where the RT primer comprises a poly(T) portion and a tail portion that comprises a universal reverse primer portion; a poly(A) polymerase, a single strand RNA ligase, and a reverse transcriptase. In certain embodiments, compositions further comprise a cDNA of a mature small RNA, the cDNA comprising the RT primer sequence at the 5' end and the adaptor sequence at the 3' end.

Certain embodiments provide for the use of any of the methods disclosed herein for the identification and/or confirmation mature small RNA biomarkers that may be used in disease detection and monitoring, treatment selection and monitoring, as well as patient diagnostic and/or prognostic methods.

BRIEF DESCRIPTION OF THE DRAWINGS

The skilled artisan will understand that the drawings described below, are for illustration purposes only. The drawings are not intended to limit the scope of the present teachings in any way.

DESCRIPTION OF EXEMPLARY EMBODIMENTS

Figure 1:
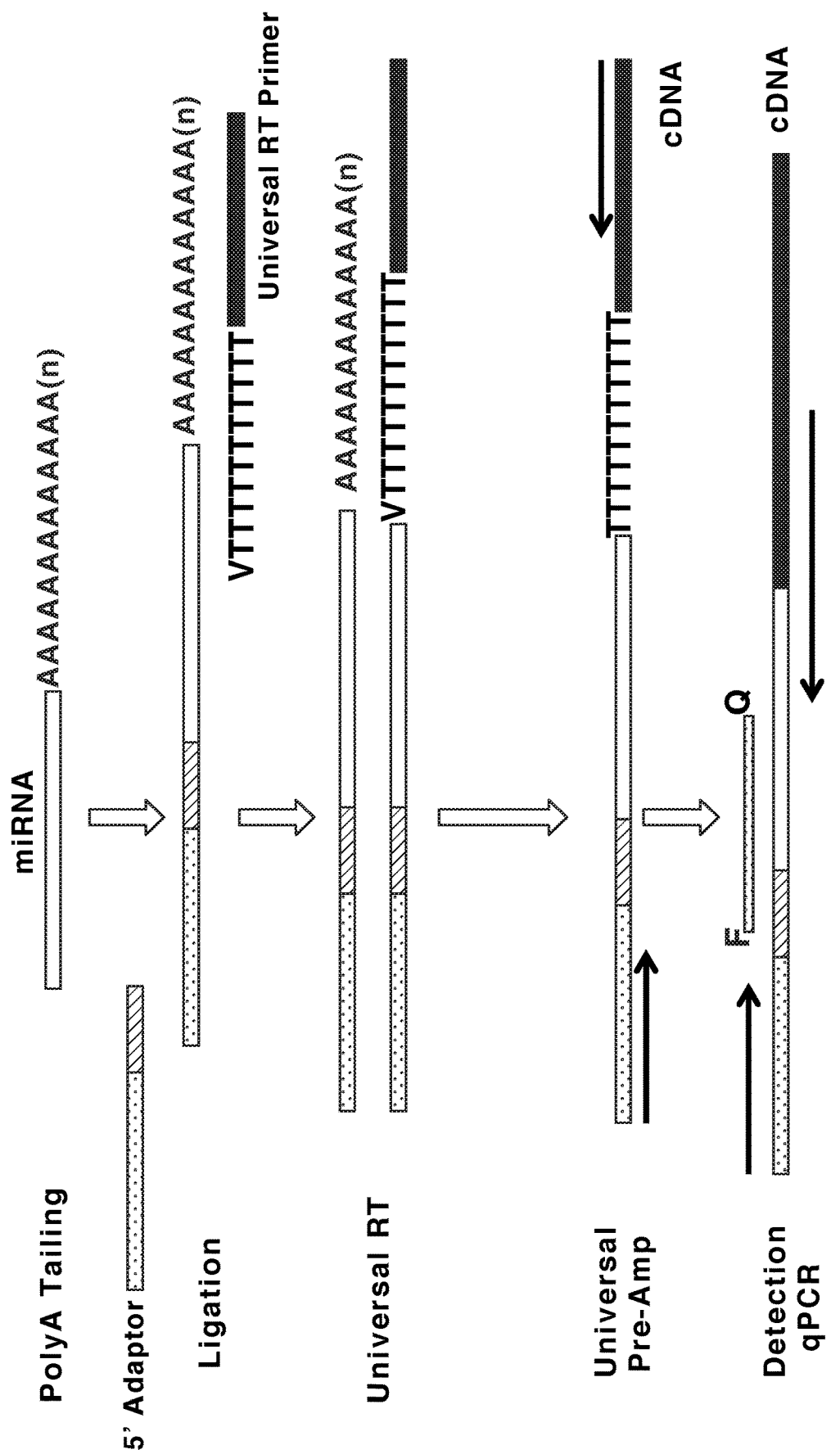
FIG. 1 schematically depicts the workflow for a two-ended universal tailing mature small RNA assay in accordance with one of the embodiments of the present teachings.

Provided herein are methods, compositions and kits for the capture and detection of target RNAs by utilizing a 5' terminal phosphate group and a 3' terminal hydroxyl group of the target RNA, such as mature small RNAs. In certain embodiments, the present teachings provide a method for capturing, detecting and quantifying a mature small RNA, such as a microRNA (miRNA), from a sample by polyadenylating the 3' end of the RNA, ligating a single-stranded universal adaptor to the 5' terminal phosphate group of the RNA, and reverse transcribing the adaptor-ligated, polyadenylated RNA with a universal reverse transcription (RT) primer. The resulting reverse transcribed product comprises the cDNA of the mature small RNA and ligated adaptor with the universal RT primer at the 5'end. This cDNA product may be captured and/or detected or, using the universal sequences added at both the 5' and 3' ends, the cDNA product may undergo universal pre-amplification (pre-amp) and/or amplification using a single pair of universal forward and reverse primers. Following such amplification reactions, the amplicons based on the target RNA may captured and/or detected. In certain embodiments, the target RNA is a mature small RNA. A non-limiting example of a workflow which includes polyadenylation, adaptor ligation, universal tailing and reverse transcription, universal pre-amplification and target mature small RNA detection by qPCR is depicted in FIG. 1. In certain embodiments, the target mature small RNA is a miRNA.

In certain embodiments, polyadenylation of the RNA may be performed before ligation of the 5' adaptor. In other embodiments, ligation of the 5' adaptor to the RNA may be performed before the polyadenylation. In certain embodiments, the ligation and the reverse transcription steps are performed together in a single reaction vessel (1-step ligation/RT). In certain embodiments, reverse transcription is catalyzed by a hot-start reverse transcriptase enzyme. Post-ligation digestion of the single-stranded universal adaptor is optional but not required. In certain embodiments, post-adaptor ligation and/or post-reverse transcription extraction, precipitation and/or clean-up is not required. In certain embodiments, successive reactions of the workflow are performed without extraction, precipitation, purification and/or other means of clean-up of the reaction products or components between the reactions steps. For example, polyadenylation, ligation, and reverse transcription can be successively performed without intervening extraction, precipitation, purification and/or other clean-up processes. In other embodiments, the polyadenylating, ligating, reverse transcribing, and pre-amplifying steps can be successively performed without intervening extraction, precipitation, purification, and/or other clean-up processes. In certain embodiments, polyadenylation, ligation, and reverse transcription can be performed in the same reaction vessel. In certain embodiments, polyadenylation, ligation, reverse transcription, and pre-amplification can be performed in the same reaction vessel. In certain embodiments, the preamplification and amplification steps are performed together in a single reaction vessel (1-step pre-amp/amplification).

Ligation of a single-stranded adaptor to the 5' end of the RNA is catalyzed by a single strand RNA ligase (sRNA ligase), such as, for example, RNA Ligase I. Ligation of the single-stranded 5' adaptor is performed in the absence of a ligation splint oligonucleotide or other sequence which hybridizes to both the adaptor and 5' end of the RNA. In certain embodiments, the single-stranded adaptor is an RNA molecule. In certain embodiments of the method, a single-stranded RNA universal adaptor is ligated to the 5' terminal phosphate group of the mature small RNA and the 3' terminal end of this RNA ligation product is polyadenylated. In some embodiments, the 5' ends of the RNA sample (the input RNA) is not modified prior to ligation of the 5' adaptor. In certain embodiments, the input RNA is not treated to remove a cap structure or triphosphate that may be present at the 5' terminus.

By polyadenylating mature small RNA molecules, a single primer comprising a poly(T) portion is used as a universal reverse transcription (RT) primer and is shared by all cDNA from the target polynucleotides in the sample. By using a universal 5' ligation adaptor and universal RT primer, each having universal primer portions, a universal primer pair can be used for pre-amplification and/or amplification (e.g., universal forward and universal reverse primers) for the mature small RNA cDNA molecules that have been modified with the adaptor and RT primer.

Ligation of the 5' ligation adaptor sequence to the mature small RNA facilitates the synthesis of a full-length cDNA of the mature small RNA ligated to the adaptor. With the adaptor ligated to the RNA's 5' end, the reverse transcription reaction proceeds to copy the complete sequence at the 5' terminal end of the mature small RNA. Accordingly, in certain embodiments, the methods and workflow provided here in detect the 5' terminal base of the target mature small RNA. In some embodiments, the methods and workflow provided here can distinguish 5' terminal isomers of the target mature small RNAs.

In certain embodiments, the 5' ligation adaptor contains sequences which facilitate entry of the cDNA or amplification products into a next generation sequencing (NGS) workflow. In some embodiments, the 5' ligation adaptor includes at least one bar code, zip code or address sequence enabling capture, sorting, or otherwise further processing the cDNA or amplification products.

In certain embodiments, the universal RT primer contains sequences which facilitate entry of the cDNA or amplification products into a next generation sequencing (NGS) workflow. In some embodiments, the universal RT primer includes at least one bar code, zip code or address sequence enabling capture, sorting, or otherwise further processing the cDNA or amplification products.

In certain embodiments, a blocking oligonucleotide may be used. In certain embodiments, a blocking oligonucleotide may be used in the ligation and/or pre-amplification steps. Detection of the target polynucleotides may be performed using amplification methods such as the polymerase chain reaction (PCR), such as quantitative real-time PCR, quantitative endpoint PCR, and standard PCR.

In certain embodiments, the sample containing a target RNA, such as a mature small RNA, may be a preparation of total RNA, a cellular or tissue extract, a biological fluid (for example, blood serum), an intact cell, an in vitro transcription reaction, or a chemical synthesis. Embodiments of the workflow provided herein are particularly useful for the detection of mature small RNA species present in low abundance and/or expressed at low levels, as well as for use in analyzing such RNA from small, rare and/or limited biological samples. For example, provided methods are of use in detecting and/or quantitating mature small RNA in RNA preparations from tissue biopsies, formalin- or paraformalin fixed paraffin-embedded tissue (FFPE), blood serum, blood plasma, and urine. As demonstrated, the methods provided herein possess high sensitivity and specificity to detect and quantitate miRNA in RNA samples with relatively low copy number.

In certain embodiments, the methods, compositions and kits provided herein are for use in detecting and/or quantitating expression of mature small RNA in biological samples. In some embodiments, the methods, compositions, and kits provided herein are for use in identifying and/or confirming small mature RNA biomarkers for disease detection and monitoring. The methods provided herein are of use in screening RNA samples from individuals or populations of varying states of health, age, or other conditions for the potential miRNA biomarkers.

The methods and compositions provided are well suited for high throughput sample preparation and analysis. For example, two-ended universal tailing of the miRNA in a total RNA sample allows the generation of a single cDNA or pre-amplification product that reflects the population of miRNA in the RNA sample and that can be assayed to identify and/or quantitate miRNA species in the RNA sample. In some embodiments, the provided methods are performed on a large number of RNA samples at the same time, such as in a high throughput process. In certain embodiments, the reaction vessels used in the workflow are wells in a 96-well plate. In certain embodiments, the reaction vessels used in the workflow are wells in a 384-well plate.

In certain embodiments, the provided methods also are amenable to detecting and/or quantitating expression of mature small RNA and other types of RNA, such as mRNA, from the same RNA sample. As described herein, the workflow can be performed without extraction or purification processes between the successive polyadenylation, ligation, reverse transcription, and/or amplification reactions. Accordingly, the reaction mixture which contains the mature small RNA cDNA product or amplification product also contains RNA that present in the sample at the beginning of the workflow. For example, following the reverse transcription step or the pre-amplification step, a portion of the reaction can be removed and used to detect and/or quantitate expression of another target RNA, such as an mRNA. Using the workflow's reaction mix for the detection and/or quantification of both types of RNA allows a correlation to be made between expression of the mature small RNA and the mRNA from the same original sample. This may be beneficial for analysis of small and/or limited RNA samples or source materials.

Methods have been described for extending the length of microRNA by polyadenylating the 3' end, reverse transcribing the polyadenylated miRNA to form cDNA, and ligating an oligonucleotide adaptor using a complementary splint oligonucleotide to the 3' end of the microRNA cDNA with a double-strand ligase. When starting with a sample containing a whole RNA transcriptome, the double strand ligation method captures the whole mix of RNAs including microRNA, ncRNA, rRNA, mRNA, and piRNAs and results in a ligated preparation with high complexity for subsequent detection and quantification. In contrast, the methods provided herein use a single strand RNA ligase which ligates only to RNA molecules having monophosphorylated 5' ends, excluding 5' capped mRNA and 5'-triphosphorylated RNA. Use of a single strand RNA ligase in the workflow provided herein improved the overall target ligation efficiency from less than 10% (with the double strand ligation method) to more than 50% and reduce ligation side-product background. Accordingly, use of the provided methods and compositions reduce the complexity of the captured product for detection and quantification. When capturing small RNAs, using adaptors with splint oligonucleotides to generate double stranded ligation requires thousands of different splint oligonucleotides or sequences to ensure sequence complementarity with the targeted small RNAs. In contrast, no splint oligonucleotides are required for ligation in the methods provided herein.

The use of the universal primers and amplification workflow provided herein gives one or more of the following advantages: 1) allows for a single-plex reaction; 2) reduces target-specific biases in ligation and amplification; 3) eliminates fixed or custom pools of target-specific primers, such as small RNA specific primers; 4) eliminates target number restriction; 5) eliminates the need for design updates based on newly discovered mature small RNA species; 6) eliminates the need for small RNA specific primer pool development and validation; and 7) simplifies manufacturing since only one set of universal primers are required to amplify a population of target RNAs, such as small RNAs. In addition, this system allows for increased flexibility for target-specific primer design and probe design since the target RNA, such as mature small RNA, can be directly detected via assay methods such as real-time PCR. Furthermore, the ability to perform successive reactions without intervening clean-up processes provides the following advantages: 1) simplifies the workflow; 2) decreases the time to results; 3) decreases the hands-on time; and 4) reduces the variation between assays.

In certain embodiments, the present teachings provide a method for detecting a miRNA in a sample, the method including: polyadenylating the 3' end of the miRNA and ligating a single-stranded universal adaptor to the 5' end of the miRNA; reverse transcribing the adaptor-ligated, polyadenylated miRNA using a universal reverse transcription (RT) primer, whereby a cDNA product is formed, wherein the universal RT primer comprises a poly(T) portion and a tail portion, the tail portion comprising a universal primer portion; amplifying the cDNA ligation product using a pair of universal forward and reverse primers; and detecting the target miRNA by PCR. In certain embodiments, the present teachings provide a method for detecting a miRNA in a sample, the method including: polyadenylating the 3' end of the miRNA and ligating a single-stranded universal adaptor to the 5' end of the miRNA; reverse transcribing the adaptor-ligated, polyadenylated miRNA using a universal reverse transcription (RT) primer, whereby a cDNA product is formed, wherein the universal RT primer comprises a poly (T) portion and a tail portion, the tail portion comprising a universal primer portion; and detecting the target miRNA by PCR. Detection of the target polynucleotides may be performed using amplification methods such as the polymerase chain reaction (PCR), such as quantitative real-time PCR, quantitative endpoint PCR, and standard PCR.

In certain embodiments, compositions are provided that comprise a blocking oligonucleotide to block adaptor-primer ligated by-product formation and/or amplification. In certain embodiments, the blocking oligonucleotide is DNA. In certain embodiments, the blocking oligonucleotide is RNA. In certain embodiments, the blocking oligonucleotide comprises a poly(A) portion. In certain embodiments, the blocking oligonucleotide comprises a blocking agent, including, but not limited to, 2'-O-methyl, acridine, a minor groove binder (MGB), and an intercalating dye compound.

To more clearly and concisely describe and point out the subject matter of the present disclosure, the following definitions are provided for specific terms which are used in the following description and the appended claims. Throughout the specification, exemplification of specific terms should be considered as non-limiting examples.

As used in this specification, the words "a" or "an" means at least one, unless specifically stated otherwise. In this specification, the use of the singular includes the plural unless specifically stated otherwise. For example, but not as a limitation, "a target nucleic acid" means that more than one target nucleic acid can be present; for example, one or more copies of a particular target nucleic acid species, as well as two or more different species of target nucleic acid. The term "and/or" means that the terms before and after the slash can be taken together or separately. For illustration purposes, but not as a limitation, "X and/or Y" can mean "X" or "Y" or "X" and "Y".

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The section headings used herein are for organizational purposes only and are not to be construed as limiting the desired subject matter in any way. All literature cited in the specification, including but not limited to, patent, patent applications, articles, books and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The term "hybridizing", including, without limitation, variations of the root words "hybridize", is used interchangeably and means the complementary nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers and probes anneal to complementary sequences are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349 (1968).

In general, whether such annealing takes place is influenced by, among other things, the length of the polynucleotides and the complementarity, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by persons of ordinary skill in the art, without undue experimentation. It will be appreciated that complementarity need not be perfect; there can be a small number of base pair mismatches that will minimally interfere with hybridization between the target sequence and the single-stranded nucleic acids of the present teachings. However, if the number of base pair mismatches is so great that no hybridization can occur under minimally stringent conditions, then the sequence is generally not a complementary target sequence. Thus, "complementarity" herein is meant that the probes or primers are sufficiently complementary to the target sequence to hybridize under the selected reaction conditions to achieve the ends of the present teachings. Preferably, annealing conditions are selected to allow the primers and/or probes to selectively hybridize with a complementary sequence in the corresponding target flanking sequence or amplicon, but not hybridize to any significant degree to different target nucleic acids or non-target sequences in the reaction composition at the second reaction temperature.

The term "minor groove binder" or "MGB" as used herein refers to a small molecule that fits into the minor groove of double-stranded DNA, sometimes in a sequence specific manner Generally, minor groove binders are long, flat molecules that can adopt a crescent-like shape and thus, fit snugly into the minor groove of a double helix, often displacing water. Minor groove binding molecules typically comprise several aromatic rings connected by bonds with torsional freedom, for example, but not limited to, furan, benzene, or pyrrole rings.

As used herein, the terms "polynucleotide", "oligonucleotide," and "nucleic acid" are used interchangeably and refer to single-stranded and double-stranded polymers of nucleotide monomers, including without limitation, 2'-deoxyribonucleotides (DNA) and ribonucleotides (RNA) linked by internucleotide phosphodiester bond linkages, or internucleotide analogs, and associated counter ions, e.g., $H^+$, $NH^{4+}$, trialkylammonium, $Mg^{2+}$, $Na^+$, and the like. A polynucleotide may be composed entirely of deoxyribonucleotides, entirely of ribonucleotides, or chimeric mixtures thereof and may include nucleotide analogs. The nucleotide monomer units may comprise any of the nucleotides described herein, including, but not limited to, nucleotides and/or nucleotide analogs. Polynucleotides typically range in size from a few monomeric units, e.g., 5-40 when they are sometimes referred to in the art as oligonucleotides, to several thousands of monomeric nucleotide units. Unless denoted otherwise, whenever a polynucleotide sequence is represented, it will be understood that the nucleotides are in the 5'-to-3' order from left to right and that "A" denotes deoxyadenosine, "C" denotes deoxycytosine, "G" denotes deoxyguanosine, "T" denotes deoxythymidine, and "U" denotes deoxyuridine, unless otherwise noted.

The term "nucleotide" refers to a phosphate ester of a nucleoside, e.g., triphosphate esters, wherein the most common site of esterification is the hydroxyl group attached at the C-5 position of the pentose.

The term "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1'-position, including 2'-deoxy and 2'-hydroxyl forms. When the nucleoside base is purine or 7-deazapurine, the pentose is attached to the nucleobase at the 9-position of the purine or deazapurine, and when the nucleobase is pyrimidine, the pentose is attached to the nucleobase at the 1-position of the pyrimidine.

The term "analog" includes synthetic analogs having modified base moieties, modified sugar moieties, and/or modified phosphate ester moieties. Phosphate analogs generally comprise analogs of phosphate wherein the phosphorous atom is in the +5 oxidation state and one or more of the oxygen atoms is replaced with a non-oxygen moiety, e.g. sulfur. Exemplary phosphate analogs include: phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH4^+$, $Na^+$. Exemplary base analogs include: 2,6-diaminopurine, hypoxanthine, pseudouridine, C-5-propyne, isocytosine, isoguanine, 2-thiopyrimidine. Exemplary sugar analogs include: 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, and bromo.

As used herein, the term "target polynucleotide" refers to a polynucleotide sequence that is sought to be detected. The target polynucleotide may be obtained from any source, and may comprise any number of different compositional components. For example, the target may be a nucleic acid (e.g., DNA or RNA), messenger RNA (mRNA), transfer RNA (tRNA), small interfering RNA (siRNA), microRNA (miRNA), or other mature small RNA, and may comprise nucleic acid analogs or other nucleic acid mimics. The target may be methylated, non-methylated, or both. The target may be bisulfite-treated and non-methylated cytosines converted to uracil. Further, it will be appreciated that "target polynucleotide" may refer to the target polynucleotide itself, as well as surrogates thereof, for example, amplification products and native sequences. In certain embodiments, the target polynucleotide is a miRNA molecule. In certain embodiments, the target polynucleotide lacks a poly-A tail. In certain embodiments, the target polynucleotide is a mature small RNA molecule. The target polynucleotides of the present teachings may be derived from any number of sources, including without limitation, viruses, archae, protists, prokaryotes and eukaryotes, for example, but not limited to, plants, fungi, and animals. These sources may include, but are not limited to, whole blood, blood plasma, blood serum, a tissue biopsy, formalin-fixed paraffin-embedded tissue, lymph, bone marrow, amniotic fluid, hair, skin, semen, urine, biowarfare agents, anal secretions, vaginal secretions, perspiration, saliva, buccal swabs, various environmental samples (for example, agricultural, water, and soil), research samples generally, purified samples generally, cultured cells and lysed cells. It will be appreciated that target polynucleotides may be isolated from samples using any of a variety of procedures known in the art, for example, the Ambion™ mirVana™ miRNA isolation kit (Thermo Fisher Scientific, Inc.), the Ambion™ mirVana™ PARIS™ RNA purification kit (Thermo Fisher Scientific, Inc.), the Ambion™ MagMAX™ mirVana™ Total RNA isolation kit (Thermo Fisher Scientific, Inc.), Applied Biosystems™ TaqMan™ MicroRNA Cells-to-CT™ Kit (Thermo Fisher Scientific, Inc.), Applied Biosystems™ TaqMan™ miRNA ABC purification kits (Thermo Fisher Scientific, Inc.), and the like. It will be appreciated that target polynucleotides may be cut or sheared prior to analysis, including the use of such procedures as mechanical force, sonication, restriction endonuclease cleavage, or any method known in the art. In general, the target polynucleotides of the present teachings will be single-stranded, though in some embodiments the target polynucleotide may be double-stranded, and a single-strand may result from denaturation.

As used herein, the term "mature small RNA" refers to a small RNA molecule generally comprising about 20-30 nucleotides that was processed from a larger RNA precursor. Typically, a mature small RNA has a 5' terminal phosphate group and a 3' terminal hydroxyl group. Several different types of small RNA molecules may be detected by the methods provided herein. Examples of mature small RNAs that may be detected include, but are not limited to, microRNA (miRNA), short interfering RNA (siRNA), short (or small) hairpin RNA (shRNA), repeat-associated siRNA (rasiRNA), transacting siRNA (tasiRNA), Piwi-interacting RNA (piRNA) and 21 U RNA. The small RNA may be encoded in the genome or may originate from an exogenous double-stranded RNA molecule. The length of the mature small RNA that may be detected by the methods described herein may vary. In certain embodiments, the mature small RNA may range from about 10 nucleotides to about 50 nucleotides in length. In certain embodiments, the mature small RNA may range from about 15 nucleotides to about 35 nucleotides in length. In other embodiments, the mature small RNA may be from about 17, 18, 19, 20, 21, 22, 23, 24, 25, 26, 27, 28, 29, 30, 31 or 32 nucleotides in length.

The amount of mature small RNA in the sample added to the ligation reaction or to the polyadenylation reaction may vary depending on the source of the RNA-containing sample. In general, any amount of mature small RNA that can be ligated to a 5' adaptor can be used in a ligation step and any amount of mature small RNA that can be polyadenylated can be used in the polyadenylation step. Typically, the amount of purified mature small RNA used per reaction volume will be less than the amount of total RNA used per reaction volume. In certain embodiments, the amount of total RNA ranges from about 100 ng to about 20 pg. In certain embodiments, the amount of total RNA ranges from about 100 ng to about 2.5 ng.

As used herein, the terms "adaptor" and "ligation adaptor" are equivalent and used interchangeably and refer to an oligonucleotide that is ligated to the 5' end of the mature small RNA (i.e., a 5' ligation adaptor). The nucleotides of the 5' ligation adaptor may be standard or natural (i.e., adenosine, guanosine, cytidine, thymidine, and uridine) as well as non-standard nucleotides. Non-limiting examples of non-standard nucleotides include inosine, xanthosine, isoguanosine, isocytidine, diaminopyrimidine and deoxyuridine. The ligation adaptors may comprise modified or derivatized nucleotides. Non-limiting examples of modifications in the ribose or base moieties include the addition, or removal, of acetyl groups, amino groups, carboxyl groups, carboxymethyl groups, hydroxyl groups, methyl groups, phosphoryl groups and thiol groups. In particular, included are 2'-O-methyl and locked nucleic acids (LNA) nucleotides. Suitable examples of derivatized nucleotides include those with covalently attached dyes, such as fluorescent dyes or quenching dyes, or other molecules such as biotin, digoxygenin, or magnetic particles or microspheres. The ligation adaptors may also comprise synthetic nucleotide analogs such as morpholinos or peptide nucleic acids (PNA). Phosphodiester bonds or phosphothioate bonds may link the nucleotides or nucleotide analogs of the linkers.

In certain embodiments, the 5' ligation adaptor is a linear oligonucleotide. In certain embodiments, the 5' ligation adaptor comprises a universal forward primer portion located upstream of the 3' end of the adaptor (herein also referred to as "universal adaptor" or "5' universal adaptor" or "universal ligation adaptor" or "5' universal ligation adaptor"). In certain embodiments, the 5' ligation adaptor is an RNA oligonucleotide. In certain embodiments, the 5' ligation adaptor comprises a universal forward primer portion at the 5' terminal region of the adaptor. The 5' ligation adaptor may have any base at the 3' end as long as it is compatible for ligation with the 5' end of a mature small RNA. In certain embodiments, the 3' terminal base of the 5' ligation adaptor is A. In certain embodiments, the 3' terminal base of the 5' ligation adaptor is C. In certain embodiments, the 3' terminal base of the 5' ligation adaptor is G. In certain embodiments, the 3' terminal base of the 5' ligation adaptor is T.

The length of the 5' ligation adaptor will vary depending upon, for example, the desired length of the ligation product and the desired features of the adaptor. In general, the 5' ligation adaptor may range from about 15 to about 30 nucleotides in length, more preferably from about 19 nucleotides to about 26 nucleotides in length. In certain embodiments, the 5' ligation adaptor may be about 15, 16, 17, 18, 19, 20, 21, 22, 23, 24, 25, 26, 27, 28, 29, or 30 nucleotides in length. In certain embodiments, the Tm of the ligation adaptor ranges from about 30° C. to about 60° C.

In certain embodiments, the 5' ligation adaptor contains a stem-loop structure (herein referred to as "5' stem-loop ligation adaptor"), wherein the 5' stem-loop ligation adaptor comprises a stem and a loop, wherein the 3' end of the adaptor is single-stranded at the time of ligation to the 5' end of the mature small RNA. In certain embodiments, the 5' stem-loop ligation adaptor is a DNA-RNA hybrid oligonucleotide. In certain embodiments, the universal forward primer portion is located in the stem portion of the 5' stem-loop ligation adaptor. In certain embodiments, the universal forward primer portion is located in the loop portion of the 5' stem-loop ligation adaptor. In certain embodiments, the universal forward primer portion is located in the stem and loop portions of the 5' stem-loop ligation adaptor.

As used herein, the term "stem" refers to the double-stranded region of the stem-loop ligation adaptor that is located between the 3' terminus and the loop. Generally, the stem is between about 10 nucleotides and about 20 nucleotides in length, more preferably the stem is between 12 and about 15 nucleotides in length. In certain embodiments, the stem is about 10, 11, 12, 13, 14, 15, 16, 17, 18, 19 or 20 nucleotides in length. As a general matter, in those embodiments in which a portion of the universal primer is encoded in the stem, the stem may be longer. In those embodiments in which a portion of the universal primer is not encoded in the stem, the stem may be shorter. Those in the art will appreciate that stems shorter than about 10 nucleotides and longer than about 20 nucleotides may be identified in the course of routine methodology and without undue experimentation such that shorter and longer stems are contemplated by the present teachings.

As used herein, the term "loop" refers to the single-stranded region of the stem-loop ligation adaptor that is located between the two complementary strands of the stem and typically the loop comprises single-stranded nucleotides, although other moieties such as modified DNA or RNA, carbon spacers such as C18, and/or polyethylene glycol (PEG) are also possible. Generally, the loop is between about 10 and about 20 nucleotides in length, more preferably the loop is between 17 nucleotides and 19 nucleotides in length. In certain embodiments, the loop is about 10, 11, 12, 13, 14, 15, 16, 17, 18, 19 or 20 nucleotides in length. As a general matter, in those embodiments in which a universal primer portion is encoded in the loop, the loop may generally be longer. In those embodiments in which a universal primer portion is not encoded in the loop, the loop my generally be shorter. Those in the art will appreciate that loops shorter than about 10 nucleotides and longer than about 20 nucleotides may be identified in the course of routine methodology without undue experimentation and that shorter and longer loops are contemplated by the present teachings.

As used herein, the term "ligation product" refers to a hybrid molecule comprising at least a 5' ligation adaptor and a mature small RNA. The ligation product is generated without the use of an oligonucleotide splint complementary to the ligation adaptor and the mature small RNA.

The universal 5' ligation adaptor sequence facilitates the synthesis of a full-length cDNA of the mature small RNA ligated to the adaptor. With the adaptor ligated to the RNA's 5' end, the reverse transcription reaction proceeds to copy the complete sequence at the 5' terminal end of the mature small RNA. The universal 5' ligation adaptor sequence facilitates pre-amplification and/or PCR amplification of the cDNA product using universal primers. To drive the ligation of the 5' ligation adaptor to mature small RNA, an excess amount of ligation adaptor is used; therefore, ligation between the two ligation adaptors may be produced as a non-specific background by-products. Use of a 5' ligation adaptor having hydroxyl groups at both the 5' and 3' ends prevents adaptor-adaptor ligation and thus limits non-specific background due to ligation between two adaptors. Ligation between free (unannealed) universal reverse transcription primers and 5' ligation adaptors may be produced as a by-product during the ligation step in the provided methods, such by-product leads to non-specific background during detection. In certain embodiments, use of a hot-start reverse transcriptase enzyme for the reverse transcription step suppresses adaptor-primer byproduct. In certain embodiments, blocking oligonucleotides are used to selectively suppress amplification and/or ligation of adaptor-primer by-product to reduce the background. DNA oligonucleotides labeled at the 5' or 3' end with blocking groups, such as acridine, MGB, 2'-O-methyl, sequence-targeted amplification restrictive (STAR) blockers, and blocking oligonucleotides comprising a poly(A) sequence, may be used in the ligation, extension and/or amplification steps. The addition of such blocking oligonucleotide was found to dramatically reduce background amplification and increase sensitivity of miRNA detection by qPCR with TaqMan™ qPCR assays.

A STAR blocker oligonucleotide comprises a STAR tag sequence at the 5' end of the oligonucleotide, the STAR tag sequence being complementary to all or a portion of another primer sequence that is used in the amplification reaction. When the STAR blocker primer is extended, the extension product comprises both the STAR tag sequence at the 5' end and the complement of the STAR tag sequence in the 3' region of the extension product. Thus, the STAR primer extension product can may fold back to self-anneal thereby forming a stem-loop structure. The stem-loop structure of the extended STAR primer excludes binding of the other primer used to amplify the target molecule, thereby inhibiting amplification of the unwanted target (for example, an adaptor-adaptor ligation product). In certain embodiments, the STAR tag sequence may comprise a portion of the amplicon internal sequence to block the annealing of another primer or the extension of a DNA polymerase. STAR primers may be used for selective amplification suppression of ligated ligation adaptors in the pre-amplification of adaptor-ligated mature small RNA or cDNA in the methods provided. STAR primers are described in U.S. Ser. No. 14/071,444, filed Nov. 4, 2013, and published as U.S. Pat. Pub. No. 2014/0134614, herein incorporated by reference in its entirety.

In certain embodiments, the blocking oligonucleotide comprises a poly(A) portion and is present during the ligation reaction. In methods in which a polyadenylated mature small RNA has an adaptor ligated at the 5' end and is reverse transcribed using a universal reverse transcription primer to generate a cDNA, the inclusion of a blocking oligonucleotide during the ligation reaction can selectively suppress formation of adaptor-universal RT primer by-product. In certain embodiments, a blocking oligonucleotide has a stem-loop structure and a poly(A) containing single-stranded overhang portion at its 3' end. In other embodiments, the blocking oligonucleotide is a linear oligonucleotide and has a poly(A) portion at its 5' end and sequences complementary to the universal reverse transcription primer at its 3' end. In certain embodiments, the non-poly(A) portion of the blocking oligonucleotide comprises deoxyuridine. In certain embodiments, the Tm of the RT primer and blockers comprising a poly(A) portion ranges from about 30° C. to about 60° C., from about 35° C. to about 50° C., or about 38° C. to about 42° C.

A "blocking group" is a chemical moiety that can be added to a nucleotide or a nucleic acid to prevent or minimize nucleotide addition by a DNA polymerase. By adding a blocking group to the terminal 3'-OH, the nucleotide is no longer able to participate in phosphodiester bond formation catalyzed by the DNA polymerase. Some non-limiting examples include, an alkyl group, non-nucleotide linkers, phosphorothioate, alkane-diol residues, PNA, LNA, nucleotide analogs comprising a 3'-amino group in place of the 3'-OH group, nucleotide analogs comprising a 5'-OH group in place of the 5'-phosphate group, nucleotide derivatives lacking a 3'-OH group, biotin, nucleic acid intercalators, acridine, and minor groove binders. An alkyl blocking group is a saturated hydrocarbon that can be straight chained, branched, cyclic, or combinations thereof. Some non-limiting examples of non-extendable nucleotides include nucleotides that have a 3'-hydroxyl group that has been modified such as by substitution with hydrogen or fluorine or by formation of an ester, amide, sulfate or glycoside. These nucleotides are generally not chain extendable. Other examples of non-extendable nucleotides that can be used include nucleotides that have modified ribose moieties. In certain embodiments, ribonucleotides may serve as non-extendable nucleotides because oligonucleotides terminating in ribonucleotides cannot be extended by certain DNA polymerases. The ribose can be modified to include 3'-deoxy derivatives including those in which the 3'-hydroxy is replaced by a functional group other than hydrogen, for example, as an azide group. In certain embodiments, a non-extendible nucleotide comprises a dideoxynucleotide (ddN), for example but not limited to, a dideoxyadenosine (ddA), a dideoxycytosine (ddC), a dideoxyguanosine (ddG), a dideoxythymidine (ddT), or a dideoxyuridine (ddU). In a preferred embodiment, the blocking group is selected from the group consisting of a minor groove binder, a 2'-O-methyl group, a biotin, an acridine, and a phosphothioate group.

Ligation of the ligation adaptors to the mature small RNA is catalyzed by a single strand RNA ligase, for example RNA ligase I. In certain embodiments, the methods, kits and compositions provided herein include a single strand RNA ligase, such as RNA Ligase I. In certain embodiments, the methods, kits and compositions provided herein include RNA Ligase I.

The conditions of the ligation reaction are typically adjusted so that the ligase functions near its optimal activity level. A buffering agent may be utilized to adjust and maintain the pH at the desired level. Representative examples of suitable buffers include, but are not limited to, MOPS, HEPES, TAPS, Bicine, Tricine, TES, PIPES, MES, sodium acetate and Tris buffer. The ligation mixture may further comprise a divalent cation. Suitable divalent cations include, but are not limited to calcium, magnesium and manganese. The reaction mixture may further comprise a reducing agent. Non-limiting examples include dithiothreitol and β-mercaptoethanol. A ribonuclease (RNase) inhibitor may also be added to the ligation mixture. The ligation mixture may further comprise ATP.

As used herein, the term "extension reaction" refers to an elongation reaction in which the 3' end of a primer sequence is hybridized to a target sequence is extended to form an "extension reaction product" comprising a strand complementary to the target polynucleotide. As used herein, "reverse transcription" is also referred to as an extension reaction. In certain embodiments, the extension reaction is a reverse transcription reaction comprising a polymerase, such as a reverse transcriptase. In some embodiments, the target polynucleotide is a polyadenylated miRNA molecule having an RNA adaptor ligated at the 5' end and the extension reaction is a reverse transcription reaction comprising a reverse transcriptase, whereby a DNA copy of the miRNA ligation product is made.

Reverse transcriptases include any enzyme having reverse transcriptase activity. Such enzymes include, but are not limited to, retroviral reverse transcriptase (e.g., Moloney Murine Leukemia Virus (M-MLV), Avian Myeloblastosis Virus (AMV) or Rous Sarcoma Virus (RSV) reverse transcriptases), Superscript I™, Superscript II™, Superscript III™, retrotransposon reverse transcriptase, hepatitis B reverse transcriptase, cauliflower mosaic virus reverse transcriptase, bacterial reverse transcriptase, Tth DNA polymerase, Taq DNA polymerase, Tne DNA polymerase, Tma DNA polymerase, and mutants, variants or derivatives thereof. In certain embodiments, the reverse transcriptase is a hot-start reverse transcriptase enzyme.

In one embodiment, reverse transcriptases include those that have reduced, substantially reduced or eliminated RNase H activity. By an enzyme "substantially reduced in RNase H activity" is meant that the enzyme has less than about 20%, 15%, 10%, 5%, or 2%, of the RNase H activity of the corresponding wild type or RNase H+ enzyme such as wild type Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al, Nucl. Acids Res. 16:265 (1988) and in Gerard, G. F., et al., FOCUS 14:91 (1992), the disclosures of all of which are fully incorporated herein by reference. Polypeptides suitable for use in the compositions and methods described herein include, but are not limited to, M-MLV H-reverse transcriptase, RSV H-reverse transcriptase, AMV H-reverse transcriptase, RAV (Rous-associated virus) H-reverse transcriptase, MAV (myeloblastosis-associated virus) H-reverse transcriptase, HIV H-reverse transcriptase, and Superscript III®, and mutants, variants or derivatives thereof. It will be understood by one of ordinary skill, however, that any enzyme capable of producing a DNA molecule from a ribonucleic acid molecule (i.e., having reverse transcriptase activity) may be equivalently used in the compositions, methods and kits described herein.

The enzymes having reverse transcriptase and/or polymerase activity may be obtained commercially, for example from Thermo Fisher Scientific's Invitrogen™ or Applied Biosystems™ Perkin-Elmer (Branchburg, N.J.), New England BioLabs (Beverly, Mass.) or Boehringer Mannheim Biochemicals (Indianapolis, Ind.). Alternatively, polymerases or reverse transcriptases having polymerase activity may be isolated from their natural viral or bacterial sources according to standard procedures for isolating and purifying natural proteins that are well-known to one of ordinary skill in the art (see, e.g., Houts, G. E., et al., J. Virol. 29:517 (1979)). In addition, such polymerases and/or reverse transcriptases may be prepared by routine recombinant DNA techniques well known to those skilled in the art (see, e.g., Kotewicz, M. L., et al., Nucl. Acids Res. 16:265 (1988); U.S. Pat. No. 5,244,797; PCT Application Pub. No. WO 98/47912; Soltis, D. A., and Skalka, A. M., Proc. Natl. Acad. Sci. USA 85:3372-3376 (1988)).

According to some embodiments, with appropriate buffers, salts, pH, temperature, and nucleotide triphosphates, including analogs thereof, i.e., under appropriate conditions, a polymerase incorporates nucleotides complementary to the template strand starting at the 3' end of an annealed ligation product, to generate a complementary strand. In some embodiments, the polymerase used for extension lacks or substantially lacks 5' exonuclease activity. In some embodiments of the present teachings, unconventional nucleotide bases may be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carry-over of previous uracil-containing products by the use of uracil-N-glycosylase (see for example PCT Application Pub. No. WO 92/01814A2). In some embodiments of the present teachings, any of a variety of techniques can be employed prior to amplification in order to facilitate amplification success, as described for example in Radstrom et al., Mol Biotechnol. 26:133-46 (2004). In some embodiments, amplification may be achieved in a self-contained integrated approach comprising sample preparation and detection, as described for example in U.S. Pat. Nos. 6,153,425 and 6,649,378. Reversibly modified enzymes, for example but not limited to those described in U.S. Pat. No. 5,773,258, are also within the scope of the disclosed teachings. The present teachings also contemplate various uracil-based decontamination strategies, wherein for example uracil may be incorporated into an amplification reaction, and subsequent carry-over products removed with various glycosylase treatments (see, for example, U.S. Pat. No. 5,536,649). Those in the art will understand that any protein with the desired enzymatic activity may be used in the disclosed methods, compositions, and kits.

In certain embodiments, the target polynucleotide is a miRNA or other mature small RNA molecule and as such it will be appreciated that the use of polymerases that also comprise reverse transcription properties can allow for some embodiments of the present teachings to comprise a first reverse transcription reaction followed thereafter by an amplification reaction, thereby allowing for the consolidation of two reactions in essentially a single reaction. In certain embodiments, the consolidation of the extension reaction and subsequent amplification reaction is further contemplated by the present teachings.

As used herein, the term "universal primer portion" refers to a region of a ligation adaptor or a universal reverse transcription (RT) primer that may serve directly, or by virtue of its complement, as the template upon which a universal primer may hybridize for any of a variety of primer nucleotide extension reactions known in the art (for example, PCR or RT-PCR). It will be appreciated by those of skill in the art that when two primer portions are present on a single polynucleotide, the orientation of the two primer portions is generally different. For example, one PCR primer may directly hybridize to a first primer portion, while the other PCR primer may hybridize to the complement of the second primer portion. In addition, "universal" primers and primer portions as used herein are generally chosen to be as unique as possible given the particular assays and host genomes to ensure specificity of the assay.

As used herein, the term "universal primer" refers to a primer that may be used in a plurality of different reactions querying different target polynucleotides and hybridizes to the universal primer portion of the ligation adaptor or universal RT primer. Generally, the region of the universal primer that hybridizes to the ligation adaptor or universal RT primer is between about 15 and about 25 nucleotides in length, more preferably between about 18 nucleotides and about 22 nucleotides in length. In certain embodiments, the region that hybridizes to the ligation adaptor or universal RT primer is about 15, 16, 17, 18, 19, 20, 21, 22, 23, 24, or 25 nucleotides in length. Those in the art will appreciate that lengths of the ligation adaptor or universal RT primer portion of the universal primer may be shorter than about 15 nucleotides and longer than about 25 nucleotides in length and may be identified in the course of routine methodology and without undue experimentation and that such longer or shorter ligation adaptor or universal RT primer portions of universal primers are contemplated by the present teachings. The universal primer may comprise standard, non-standard, derivatized and modified nucleotides as described herein.

As used herein, the term "universal reverse transcription (RT) primer" refers to a primer that may be used in a plurality of different reactions querying different target polynucleotides. The universal RT primer comprises a poly(T) portion and a tail portion, wherein the tail portion comprises a universal primer portion. Typically, the poly(T) portion is at the 3' end of the universal RT primer. In certain embodiments, the poly(T) sequence at the 3' end of the primer is followed by one additional nucleotide base which is not a T. Generally, the universal RT primer is between about 15 and 25 nucleotides in length, more preferably between about 18 nucleotides and about 22 nucleotides in length. In certain embodiments, the universal RT primer is about 15, 16, 17, 18, 19, 20, 21, 22, 23, 24 or 25 nucleotides in length. The universal RT primer may comprise standard, non-standard, derivatized and modified nucleotides as described herein above.

As used herein, the term "universal forward primer" refers to a primer that may be used in a plurality of different reactions querying different target polynucleotides. As used herein, the term "universal reverse primer" refers to a primer that may be used in a plurality of different reactions querying different target polynucleotides. In a typical PCR amplification, forward and reverse primers are used to preferentially target and amplify a DNA sequence of interest. As used in the provided methods, a single pair of universal forward and reverse primers allows amplification of different target polynucleotides since the target polynucleotides are modified to include universal primer portions that serve directly, or by virtue of its complement, as a template upon which a universal forward or reverse primer may hybridize.

In certain embodiments, the universal forward primer hybridizes to a portion of the 5' ligation adaptor that comprises the universal primer portion or complement of the universal primer portion. Generally, the region of the universal forward primer that hybridizes to the 5' ligation adaptor is between about 15 and about 25 nucleotides in length, more preferably between about 18 nucleotides and about 22 nucleotides in length. In certain embodiments, the region that hybridizes to the 5' ligation adaptor is about 15, 16, 17, 18, 19, 20, 21, 22, 23, 24, or 25 nucleotides in length. Those in the art will appreciate that lengths of the 5' ligation adaptor portion of the universal forward primer may be shorter than about 15 nucleotides and longer than about 25 nucleotides in length and may be identified in the course of routine methodology and without undue experimentation and that such longer or shorter 5' ligation adaptor portions of universal forward primers are contemplated by the present teachings. The universal forward primer may comprise standard, non-standard, derivatized and modified nucleotides as described herein above.

In certain embodiments, the universal reverse primer hybridizes to a portion of the universal RT primer comprising the universal primer portion or its complement. Following the reverse transcription reaction, the universal forward primer may be extended to form a second strand product. The universal reverse primer may hybridize with this second strand and may be extended to continue the amplification reaction. Generally, the universal reverse primer is between about 15 and 25 nucleotides in length, more preferably between about 18 nucleotides and about 22 nucleotides in length. In certain embodiments, the universal reverse primer is about 15, 16, 17, 18, 19, 20, 21, 22, 23, 24 or 25 nucleotides in length. The universal reverse primer may comprise standard, non-standard, derivatized and modified nucleotides as described herein above.

The term "upstream" as used herein takes on its customary meaning in molecular biology, and refers to the location of a region of a polynucleotide that is on the 5' side of a "downstream" region. Correspondingly, the term "downstream" refers to the location of a polynucleotide that is on the 3' side of an "upstream" region.

The terms "amplicon" and "amplification product" as used herein generally refer to the product of an amplification reaction. An amplicon may be double-stranded or single-stranded, and may include the separated component strands obtained by denaturing a double-stranded amplification product. In certain embodiments, the amplicon of one amplification cycle can serve as a template in a subsequent amplification cycle.

As used herein, the term "amplifying" refers to any means by which at least a part of a target polynucleotide, target polynucleotide surrogate, or combinations thereof, is reproduced, typically in a template-dependent manner, including without limitation, a broad range of techniques for amplifying nucleic acid sequences, either linearly or exponentially. Any of several methods can be used to amplify the target polynucleotide. Any in vitro means for multiplying the copies of a target sequence of nucleic acid can be utilized. These include linear, logarithmic, or any other amplification method. Exemplary methods include polymerase chain reaction (PCR; see, e.g., U.S. Pat. Nos. 4,683,202; 4,683,195; 4,965,188; and 5,035,996), isothermal procedures (using one or more RNA polymerases (see, e.g., PCT Application Publication No. WO 2006/081222), strand displacement (see, e.g., U.S. Pat. No. RE39,007), partial destruction of primer molecules (see, e.g., PCT Application Publication No. PCT Application Publication No. WO 2006/087574)), ligase chain reaction (LCR) (see, e.g., Wu, et al. Genomics 4:560-569 (1990) and Barany, et al. Proc. Natl. Acad. Sci. USA 88:189-193 (1991)), Qβ RNA replicase systems (see, e.g., WO 1994/016108), RNA transcription-based systems (e.g., TAS, 3SR), rolling circle amplification (RCA) (see, e.g., U.S. Pat. No. 5,854,033; U.S. Pat. Application Publication No. 2004/265897; Lizardi, et al. Nat. Genet. 19:225-232 (1998); and Banér, et al. Nucleic Acid Res. 26: 5073-5078 (1998)), and strand displacement amplification (SDA) (Little, et al. Clin. Chem. 45:777-784 (1999)), among others. Many systems are suitable for use in amplifying target nucleic acids and are contemplated herein as would be understood by one of skill in the art.

As described herein, in certain embodiments, the present teachings provide a method for detecting a mature small RNA which includes a pre-amplification step in the workflow. During the pre-amplification step, a limited number of cycles of amplification occur (for example, but not limited to 2, 3, 4, 5, 6, 7, 8, 9, 10, 11, 12, 13, 14, or 15 cycles of amplification). Generally, the resulting amplicon is then diluted and portions of the diluted amplicon are subjected to additional cycles of amplification in a subsequent amplification step (see, for example, U.S. Pat. Nos. 6,606,451 and 8,815,546), or otherwise analyzed for the pre-amplified target. In certain embodiments, a pre-amplification step is performed with a pair of universal forward and reverse primers for 2-18 cycles. In certain embodiments, a pre-amplification step is performed with a pair of universal forward and reverse primers for 2-14 cycles. In some embodiments, 5-12 cycles of pre-amplification is performed. In some embodiments, 10-14 cycles of pre-amplification is performed.

As demonstrated herein, inclusion of a pre-amplification step in the provided methods for detecting and/or quantitating a mature small RNA can provide a significant improvement in detection sensitivity as compared to the methods performed without the pre-amplification step. In some embodiments, inclusion of a pre-amplification step in the workflow prior to real-time PCR detection improves sensitivity of the assay about 3 to 10 Ct's compared to performance of the workflow and assay without pre-amplification.

In some embodiments, inclusion of a pre-amplification step in the workflow prior to real-time PCR detection improves sensitivity of the assay about 6 to 10 Ct's compared to performance of the workflow and assay without pre-amplification. In some embodiments, inclusion of a pre-amplification step in the workflow prior to real-time PCR detection improves sensitivity of the assay up to about 1000-fold compared to performance of the workflow and assay without pre-amplification. In some embodiments, inclusion of a pre-amplification step in the workflow prior to real-time PCR detection improves sensitivity of the assay up to about 10-fold, about 50-fold, about 100-fold, about 500-fold, about 1000-fold compared to performance of the workflow and assay without pre-amplification.

In certain embodiments, the methods provided herein further include assaying the cDNA product comprising the cDNA of the mature small RNA and the 5' ligation adaptor, or the pre-amplification product comprising amplicons of the cDNA product, such that the mature small RNA's cDNA or the cDNA amplicons are detected. The assays may be quantitative, such that the amount or copies of the mature small RNA in a sample may be determined. Alternatively, the assays may be qualitative, such that the presence of a mature small RNA may be determined in the sample, but its level may not be measured. Furthermore, the assays may be such that the mature small RNA or its cDNA or cDNA amplicons may be isolated from the sample for further study.

In certain embodiments, an amplification method may be used to assay the cDNA or pre-amplified product. Non-limiting examples of suitable amplification methods include quantitative real-time PCR, quantitative end-point PCR and standard PCR. To assay the cDNA or pre-amplified product in certain embodiments, the amplification method may use a forward primer having a small RNA-specific portion and a universal reverse primer, and the detection of the amplified cDNA may be through use of a probe having a small RNA-specific portion. In certain embodiments, the assay amplification method may use a universal forward primer and a reverse primer having a small RNA-specific portion, and the detection of the amplified cDNA may be through use of a small RNA-specific probe. In certain embodiments, the assay amplification method may use universal forward and reverse primers, and the detection of the amplified cDNA may be through use of a small RNA-specific probe. In certain embodiments, the assay amplification method may use a forward primer having a small RNA-specific portion and a universal reverse primer, and the detection of the amplified cDNA may be through use of a universal probe. In certain embodiments, the assay amplification method may use a forward primer having a small RNA-specific portion and a reverse primer having a small RNA-specific portion, and the detection of the amplified cDNA may be through use of a small RNA-specific probe.

In certain embodiments, the set of primers and probe used to assay the cDNA or pre-amplified products are configured to detect the 5' and/or 3' ends of the target mature small RNA. For example, in certain embodiments, the forward primer or probe hybridizes to the portion of the cDNA comprising the junction between the ligated adaptor and the 5' end of the mature small RNA. In certain embodiments, the reverse primer or probe hybridizes to the portion of the cDNA comprising the junction between the poly(A) addition and the 3' end of the mature small RNA. In such embodiments, sequences at the 5' and/or 3' ends of the mature small RNA can be queried and terminal isomers detected. The extension of the 5' and 3' ends of the mature small RNA in the workflow and detection assays provided herein permit the discrimination of mature small RNA isomers, including isomers that differ at their termini.

The universal forward and reverse primers and probes and the small RNA-specific forward and reverse primers and probes may comprise standard, nonstandard, derivatized and modified nucleotides as detailed above. The forward and reverse primers may each range from about 15 to about 25 nucleotides in length, and in certain embodiments, from about 18 nucleotides to about 22 nucleotides in length.

In certain embodiments, quantitative real-time PCR (qPCR) may be used to assay the ligation product. In this method, the amount of PCR product is followed cycle-by-cycle in real time. To measure the amount of PCR product, the reaction may be performed in the presence of a fluorescent dye whose fluorescence increases greatly when bound to double-stranded DNA. Non-limiting examples of suitable fluorescent dyes include SYBR™ Green I, PicoGreen™ I, EvaGreen™, ethidium bromide and acridine orange. The reaction may also be performed with a fluorogenic reporter probe that is specific for the DNA being amplified. Non-limiting examples of reporter probes include TaqMan™ probes, molecular beacons, and Scorpion™ primers. The aforementioned probes depend on Förster Resonance Energy Transfer (FRET) to quench the fluorescence signal via the coupling of a fluorogenic dye molecule and a quencher moiety on the same or different oligonucleotide substrates. The fluorescence signal is generated when the fluorogenic dye molecule and the quencher are decoupled via enzymatic or physical means. Fluorescence values are generally recorded during each cycle and represent the amount of product amplified to that point in the amplification reaction. The cycle during which the fluorescence exceeds a defined threshold value is defined as the threshold cycle (Ct). In general, the amount of starting material may be calculated by determining the Ct value of the sample and comparing it to Ct value of control samples.

In certain embodiments, quantitative end-point PCR may also be used to assay the ligation product. This method is similar to qPCR in that the reaction is generally performed in the presence of a fluorescent dye or a fluorogenic probe and/or primer, but the amount of PCR product is not followed cycle-by-cycle. Rather the PCR product is analyzed at the end of the reaction by resolving the amplified product by electrophoresis on a DNA chip, an agarose gel, or a capillary, and then measuring the fluorescence of the product. The reaction typically includes a co-amplified internal control or a co-amplified synthetic nucleic acid for sample normalization.

In certain embodiments, a standard PCR method may also be used to assay the ligation product. Standard PCR procedures are well known in the art and information regarding these may be found in Ausubel et al. Current Protocols in Molecular Biology, John Wiley and Sons, NY, 1998; Ausubel et al, PCR Protocols: A Guide to Methods and Applications, Academic Press, NY, 1990 or Sambrook et al. Molecular Protocols: A Laboratory Manual, 3rd ed., Cold Spring Harbor Press, NY, 2001.

In one embodiment, the amplification reaction is a 5'-nuclease assay (also commercially known as TaqMan™ assays) performed using a nucleic acid polymerase, such as DNA polymerase, RNA polymerase, and reverse transcriptase, at least one oligonucleotide primer capable of specifically hybridizing to a target polynucleotide (from which the amplified target nucleic acid is amplified), at least one detectable probe that hybridizes to the amplified target nucleic acid, and which may be incorporated into the at least one primer), and at least one detectable nucleic acid binding agent (e.g., an intercalating or non-intercalating dye) which may be introduced before, during or after amplification. The probe typically contains a detectable label emitting a signal that may be monitored to ascertain whether the target nucleic acid has been amplified. In some embodiments, the probe is an oligonucleotide that hybridizes to the target nucleic acid 3' relative to the at least one primer. In some embodiments, the polymerase has nuclease activity (i.e., 5'-to-3' nuclease activity) for releasing the probe from the amplified nucleic acid. In some embodiments, release from the amplified nucleic acid renders the probe detectable. In some embodiments, the probe comprises a detectable label and a quencher molecule that quenches the detectable label when free but does not quench when the probe is hybridized to the amplified nucleic acid. In some embodiments, two or more probes may be used where at least one probe has a detectable label and at least one other probe has a quencher molecule. When in sufficiently close proximity to one another, the quencher molecule typically suppresses the signal of the detectable label on the other probe. In some embodiments, two or more probes, each having a different detectable label, can be used without quencher molecules. In such embodiments, the probes are rendered detectable, either de novo or by exhibiting a different signal than either probe alone, when in sufficiently close proximity to one another. Typically, the detectable label and quencher molecule are part of a single probe. As amplification proceeds, the polymerase digests the probe to separate the detectable label from the quencher molecule. The detectable label (e.g., fluorescence) is monitored during the reaction, where detection of the label corresponds to the occurrence of nucleic acid amplification (i.e., the higher the signal the greater the amount of amplification). Variations of TaqMan™ assays, such as LNA™ spiked TaqMan™ assay, are known in the art and would be suitable for use in the methods described herein.

Any of several methods can be used to detect amplified target nucleic acids using primers or probes. Many different reagents, systems, or detectable labels can be used in the methods described herein. These include, for example, TaqMan™ systems, detectable label-quencher systems (e.g., FRET, salicylate/DTPA ligand systems (see, e.g., Oser, et al. Angew. Chem. Int. Ed. Engl. 29:1167-1169 (1990), displacement hybridization, homologous probes, assays described in EP 070685), molecular beacons (e.g., NASBA™), locked nucleic acid (LNA) bases (Singh, et al. Chem. Commun 4:455-456 (1998)), peptide nucleic acid (PNA) probes (Pellestor, et al. Eur. J. Hum. Gen. 12:694-700 (2004)), Eclipse probes (Afonina, et al. Biotechniques 32:940-949 (2002)), light-up probes (Svanvik, et al. Anal. Biochem. 281:26-35 (2000)), molecular beacons (Tyagi, et al. Nat. Biotechnol. 14:303-308 (1996)), tripartite molecular beacons (Nutiu, et al. Nucleic Acids Res. 30:E94 (2002)), QuantiProbes (www.qiagen.com), HyBeacons (French, et al. Mol. Cell. Probes 15:363-374 (2001)), displacement probes (Li, et al. Nucleic Acids Res. 30:E5 (2002)), HybProbes (Cardullo, et al. Proc. Natl. Acad. Sci. USA 85:8790-8794 (1988)), MGB Alert (www.nanogen.com), Q-PNA (Fiandaca, et al. Genome Res. 11:609-613 (2001)), Plexor (Promega), LUX™ primers (Nazarenko, et al. Nucleic Acids Res. 30:E37 (2002)), Scorpion™ primers (Whitcombe, et al. Nat. Biotechnol. 17:804-807 (1999)), AmpliFluor™ (Sunrise) primers (Nazarenko, et al. Nucleic Acids Res. 25:2516-2521 (1997)), DzyNA primers (Todd, et al. Clin. Chem. 46:625-630 (2000)), and the like. In each of these assays, the generation of amplification products can be monitored while the reaction is in progress. An apparatus for detecting the signal generated by the detectable label can be used to detect, measure, and quantify the signal before, during, or after amplification. The particular type of signal may dictate the choice of detection method. For example, in some embodiments, fluorescent dyes are used to label probes or amplified products. The probes bind to single-stranded or double-stranded amplified products, or the dyes intercalate into the double-stranded amplified products, and consequently, the resulting fluorescence increases as the amount of amplified product increases. The use of other methods or reagents is also contemplated herein as would be understood by one of skill in the art.

Another exemplary system utilizes double-stranded probes in displacement hybridization methods (see, e.g., Morrison, et al. Anal. Biochem. 183:231-244 (1989); and Li, et al. (supra)). In such methods, the probe typically includes two complementary oligonucleotides of different lengths where one includes a detectable label and the other includes a quencher molecule. When not bound to a target nucleic acid, the quencher suppresses the signal from the detectable label. The probe becomes detectable upon displacement hybridization with a target nucleic acid. Multiple probes can be used, each containing different detectable labels, such that multiple target nucleic acids can be queried in a single reaction.

Additional exemplary methods for amplifying and detecting target nucleic acids involve "molecular beacons", which are single-stranded hairpin shaped oligonucleotide probes. In the presence of the target sequence, the probe unfolds, binds and emits a signal (e.g., fluoresces). A molecular beacon typically includes at least four components: 1) the "loop", an 18-30 nucleotide region which is complementary to the target sequence; 2) two 5-7 nucleotide "stems" found on either end of the loop and being complementary to one another; 3) at the 5' end, a detectable label; and 4) at the 3' end, a quencher molecule that prevents the detectable label from emitting a single when the probe is in the closed loop shape (i.e., not bound to a target nucleic acid). Thus, in the presence of a complementary target, the "stem" portion of the beacon separates out resulting in the probe hybridizing to the target. Other types of molecular beacons are also known and can be suitable for use in the methods described herein. Molecular beacons can be used in a variety of assay systems. One such system is nucleic acid sequence-based amplification (NASBA™), a single step isothermal process for amplifying RNA to double stranded DNA without temperature cycling. A NASBA™ reaction typically requires avian myeloblastosis virus (AMV), reverse transcriptase (RT), T7 RNA polymerase, RNase H, and two oligonucleotide primers. After amplification, the amplified target nucleic acid can be detected using a molecular beacon. Other uses for molecular beacons are known in the art and would be suitable for use in the methods described herein.

The Scorpion™ system is another exemplary assay format that may be used in the methods described herein. Scorpion™ primers are bi-functional molecules in which a primer is covalently linked to the probe, along with a detectable label (e.g., a fluorophore) and a quencher. In the presence of a target nucleic acid, the detectable label and the quencher separate which leads to an increase in signal emitted from the detectable label. Typically, a primer used in the amplification reaction includes a probe element at the 5' end along with a "PCR blocker" element (such as an HEG monomer) at the start of the hairpin loop. The probe typically includes a self-complementary stem sequence with a detectable label at one end and a quencher at the other. In the initial amplification cycles, the primer hybridizes to the target and extension occurs due to the action of polymerase. The Scorpion™ system can be used to examine and identify point mutations using multiple probes with different tags to distinguish between the probes. Using PCR as an example, after one extension cycle is complete, the newly synthesized target region is attached to the same strand as the probe. Following the second cycle of denaturation and annealing, the probe and the target hybridize. The hairpin sequence then hybridizes to a part of the newly produced PCR product. This results in the separation of the detectable label from the quencher and causes emission of the signal. Other uses for Scorpion™ primers are known in the art and would be suitable for use in the methods described herein.

One or more detectable labels or quenching agents are typically attached to a primer or probe. The detectable label may emit a signal when free or when bound to one the target nucleic acid. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any of several detectable labels may be used to label the primers and probes used in the methods described herein. As mentioned above, in some embodiments the detectable label can be attached to a probe which may be incorporated into a primer or may otherwise bind to amplified target nucleic acid (for example, a detectable nucleic acid binding agent such as an intercalating or non-intercalating dye). When using more than one detectable label, each label should differ in its spectral properties such that the labels may be distinguished from each other, or such that together the detectable labels emit a signal that is not emitted by either detectable label alone. Exemplary detectable labels include, but are not limited to, a fluorescent dye or fluorophore (i.e., a chemical group that may be excited by light to emit fluorescence or phosphorescence), "acceptor dyes" capable of quenching a fluorescent signal from a fluorescent donor dye, and the like.

Suitable detectable labels include, for example, fluoresceins (e.g., 5-carboxy-2,7-dichlorofluorescein; 5-Carboxyfluorescein (5-FAM); 5-HAT (Hydroxy Tryptamine); 6-HAT; 6-JOE; 6-carboxyfluorescein (6-FAM); FITC); Alexa fluors (e.g., 350, 405, 430, 488, 500, 514, 532, 546, 555, 568, 594, 610, 633, 635, 647, 660, 680, 700, 750); BODIPY™ fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP, EGFP), blue fluorescent protein (e.g., BFP, EBFP, EBFP2, Azurite, mKalamal), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY™ FL/BODIPY™ FL, Fluorescein/QSY7 and QSY9), LysoTracker™ and LysoSensor™ (e.g., LysoTracker™ Blue DND-22, LysoTracker™ Blue-White DPX, LysoTracker™

Yellow HCK-123, LysoTracker™ Green DND-26, LysoTracker™ Red DND-99, LysoSensor™ Blue DND-167, LysoSensor™ Green DND-189, LysoSensor™ Green DND-153, LysoSensor™ Yellow/Blue DND-160, LysoSensor Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, 5-ROX (carboxy-X-rhodamine), Sulphorhodamine B can C, Sulphorhodamine G Extra, Tetramethylrhodamine (TRITC), WT), Texas Red, Texas Red-X, VIC and other labels described in, e.g., US Pub. No. 2009/0197254), among others as would be known to those of skill in the art. Other detectable labels can also be used (see, e.g., U.S. Pat. Application Pub. No. 2009/0197254), as would be known to those of skill in the art.

As used herein "polymerase" refers to any enzyme having a nucleotide polymerizing activity. Polymerases (including DNA polymerases and RNA polymerases) useful in accordance with the present teachings include, but are not limited to, commercially available or natural DNA-directed DNA polymerases, DNA-directed RNA polymerases, RNA-directed DNA polymerases, and RNA-directed RNA polymerases. Polymerases used in accordance with the invention may be any enzyme that can synthesize a nucleic acid molecule from a nucleic acid template, typically in the 5' to 3' direction.

Exemplary DNA polymerases that may be used in the methods, kits and compositions provided herein include, but are not limited to: *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), and mutants, and variants and derivatives thereof. RNA polymerases such as T3, T5 and SP6 and mutants, variants and derivatives thereof may also be used in accordance with the present teachings. Generally, any type I DNA polymerase may be used in accordance with the present teachings although other DNA polymerases may be used including, but not limited to, type III or family A, B, C etc., DNA polymerases.

The nucleic acid polymerases used in the methods, kits and compositions provided herein may be mesophilic or thermophilic. Exemplary mesophilic DNA polymerases include T7 DNA polymerase, T5 DNA polymerase, Klenow fragment DNA polymerase, DNA polymerase III and the like. Exemplary thermostable DNA polymerases include Taq, Tne, Tma, Pfu, Tfl, Tth, Stoffel fragment, VENT™ and DEEPVENT™ DNA polymerases, and mutants, variants and derivatives thereof (U.S. Pat. Nos. 5,436,149; 4,889,818; 4,965,188; 5,079,352; 5,614,365; 5,374,553; 5,270,179; 5,047,342; and 5,512,462; PCT Application Publication Nos. WO 92/06188, WO 92/06200, and WO 96/10640; Barnes, Gene 112:29-35 (1992); Lawyer, et al., PCR Meth. Appl. 2:275-287 (1993); Flaman, et al., Nucl. Acids Res. 22:3259-3260 (1994)). Examples of DNA polymerases substantially lacking in 3' exonuclease activity include, but are not limited to, Taq, Tne (exo-), Tma (exo-), Pfu (exo-), Pwo (exo-) and Tth DNA polymerases, and mutants, variants and derivatives thereof.

DNA polymerases for use in the present teachings may be obtained commercially, for example, from Invitrogen™ (Thermo Fisher Scientific, Inc., Carlsbad, Calif.), Pharmacia (Piscataway, N.J.), Sigma (St. Louis, Mo.) and Boehringer Mannheim. Exemplary commercially available DNA polymerases for use in the present disclosure include, but are not limited to, Tsp DNA polymerase from Invitrogen™ (Thermo Fisher Scientific, Inc., Carlsbad, Calif.).

In certain embodiments, the provided methods can be used to detect a rare mature small RNA in a sample and/or distinguish one small RNA from other similar or highly homologous small RNAs in the sample. In certain embodiments, methods for amplifying target nucleic acids use activation by polyphosphorolysis (APP) reactions to provide highly-specific amplification of the target mature small RNA or cDNA thereof. Polyphosphorolysis refers to the removal of a non-extendable nucleotide from a nucleic acid (e.g., an oligonucleotide) in the presence of one or more polyphosphorolyzing agents and an enzyme that exhibits polyphosphorolyzing activity. In certain embodiments, the polyphosphorolysis-activatable oligonucleotide (APP oligonucleotide) is a target specific oligonucleotide with a dideoxynucleotide at the 3' terminus. The 3' terminal dideoxynucleotide inhibits direct extension by polymerase but can be removed by polyphosphorolysis in the presence of a polyphosphorolyzing agent and the complementary strand of the target. Generally, the dideoxynucleotide is not removed if there is a mismatch between the APP oligonucleotide and its hybridization partner. Typically, the APP oligonucleotide is designed to have a nucleotide near the 3' end which distinguishes one target from another, for example, one miRNA from another miRNA. APP may be used to polymerize and/or amplify nucleic acid molecules, including but not limited to ribonucleic acid (e.g., RNA) and/or deoxyribonucleic acid (e.g., DNA), or hybrids thereof. APP reactions and such uses thereof are described in U.S. Pat. No. 8,932,813, herein incorporated by reference in its entirety.

APP provides for the extension of oligonucleotides by converting a non-extendable oligonucleotide into an extendable oligonucleotide, extending the oligonucleotide to produce a desired nucleic acid strand (e.g., a complementary copy of a target nucleic acid), and optionally amplifying and detecting the desired nucleic acid strand. A non-extendable nucleotide refers to a nucleotide, which upon incorporation into a nucleic acid prevents further extension of the nucleic acid, e.g., by at least one biocatalyst (e.g., enzyme). A nucleotide may be extendable by one enzyme, but non-extendable by another enzyme. A non-extendable nucleotide to one enzyme could become extendable or partially extendable under different conditions. An extendable nucleotide may refer to a nucleotide to which at least one other nucleotide can be added or covalently bonded at a 3'-position of the sugar moiety of the extendable nucleotide by a biocatalyst (e.g., enzyme) present in the reaction. Extension may also start from 2'-OH of a nucleotide which may or may not have an extendable 3'-OH. Extending a nucleic acid refers to the addition of or incorporation of one or more nucleotides to or into a given nucleic acid. An extended oligonucleotide is typically an oligonucleotide (e.g., a primer nucleic acid) to which one or more additional nucleotides have been added or otherwise incorporated (e.g., covalently bonded to). APP is typically carried out using the steps of: (a) annealing to a nucleic acid a first oligonucleotide which has a non-extendable 3' end ("P*") that is removable by polyphosphorolysis (i.e., activatable); (b) removing that 3' non-extendable terminus using a polyphosphorolyzing agent and a biocatalyst (i.e., a DNA polymerase) having polyphosphorolysis activity to produce an unblocked oligonucleotide; and, (c) extending the unblocked oligonucleotide to produce a desired nucleic acid strand. Further steps of detecting the desired nucleic acid strand may also be included as described below.

In certain embodiments, the APP method is used for miRNA-specific amplification. The nucleic acid template strand is typically a sense or antisense cDNA strand of one species of miRNA and is present in mixture with the corresponding (sense or antisense) cDNA strand of other miRNA species. The activatable (e.g., non-extendable) oligonucleotide P* has no mismatches near the 3' terminus of the target miRNA cDNA sequence and has at least one nucleotide at or near its 3' terminus that mismatches the corresponding nucleotide of the non-target miRNA species cDNA. Because of the mismatch, in step (a) of the APP method the terminal non-extendable nucleotide of oligonucleotide P* is not hybridized to the non-target miRNA cDNA. In step (b), polyphosphorolysis does not substantially remove the non-hybridized terminal or near terminal nucleotide from the activatable oligonucleotide P* annealed to the non-target miRNA. In step (c), therefore, the oligonucleotide P* is not substantially extended by polymerization on the non-target miRNA cDNA. As a result, the desired nucleic acid strand of the target miRNA cDNA synthesized on the template strand is amplified preferentially over any nucleic acid strand synthesized on the non-target miRNA cDNA. In one embodiment, the APP method is used for exponential amplification of a specific (target) miRNA species in a mixture containing one or more other (non-target) miRNA species. Following the generation of a polyadenylated miRNA ligation product and subsequent reverse transcription to create a cDNA as described herein, strands of the cDNAs may be separated to provide single-stranded DNA, followed by the serial steps (a)-(e):

(a) Annealing to the sense or antisense strands of the target and non-target cDNA a complementary activatable 2'-deoxyoligonucleotide P* that has a non-extendable 2',3'-dideoxynucleotide at its 3' terminus P* has no nucleotides at or near its 3' terminus that mismatch the corresponding 2'-deoxynucleotides on the target cDNA, but has at least one nucleotide at or near its 3' terminus that mismatches the corresponding 2'-deoxynucleotide on the non-target cDNA. Consequently, the terminal 2',3'-dideoxynucleotide is hybridized to the target strand but not to the non-target strand when the oligonucleotide P* is annealed. Simultaneously, a second 2'-deoxyoligonucleotide that is complementary to the anti-parallel strands of each cDNA is annealed to the anti-parallel strands. The activatable 2'-deoxyoligonucleotide P* and the second 2'-deoxyoligonucleotide flank the region of the cDNA to be amplified.

(b) Polyphosphorolyzing the activatable P* that is annealed to a target cDNA strand with at least one polyphosphorolyzing agent and an enzyme that has polyphosphorolysis activity. This activates the P* that is annealed to the target strand by removal of the hybridized terminal 2',3'-dideoxynucleotide. It does not substantially activate the P* that is annealed to the non-target cDNA strand because the non-hybridized terminal 2',3'-dideoxynucleotide is not substantially removed by the polyphosporolysis.

(c) Polymerizing by extending the activated oligonucleotide P* on the target strand in presence of four nucleoside triphosphates and a DNA polymerase and simultaneously extending the second 2'-deoxyoligonucleotide on both target and non-target cDNA anti-parallel strands.

(d) Separating the extension products of step (c);

(e) Repeating steps (a)-(d) until the desired level of exponential amplification of the target cDNA has been achieved.

When used to amplify DNA, the non-extendable, activatable oligonucleotide P* is typically a 2'-deoxyoligonucleotide, the terminal deoxynucleotide may be a 2',3'-dideoxynucleotide, the four nucleoside triphosphates are 2'-deoxynucleoside triphosphates, and the nucleic acid polymerase is a DNA polymerase. The DNA polymerase used in step (c) can also be the enzyme having polyphosphorolysis activity used in step (b). Amplification by APP may be linear or exponential. Linear amplification is obtained when the activatable oligonucleotide P* is the only complementary oligonucleotide used. Exponential amplification is obtained when a second oligonucleotide is present that is complementary to the desired nucleic acid strand (e.g., as in PCR). The second oligonucleotide can either be an extendable or an activatable non-extendable oligonucleotide. The activatable oligonucleotide P* and the second oligonucleotide flank the region that is targeted for amplification. In step (a), the second oligonucleotide anneals to the separated desired nucleic acid strand product of step (d). In step (c), polymerization extends the second oligonucleotide on the desired nucleic acid strand to synthesize a copy of the nucleic acid template strand. In step (d), the synthesized nucleic acid template strand is separated from the desired nucleic acid strand. Steps (a) through (d) may then be repeated until the desired level exponential amplification has been achieved.

APP methods, reactions, and compositions for use therein described in U.S. Pat. No. 8,932,813 are incorporated herein by reference. In some embodiments using APP, the one or more polyphosphorolyzing agents include those represented by Formula I or Formula II of U.S. Pat. No. 8,932,813 including, but not limited to, a diphosphate, a triphosphaste, a tetraphosphate, a pentaphosphate or a hexaphosphate. For example, imidodiphosphate links the phosphate moieties using nitrogen; similar diphosphate compounds may substitute sulfur for nitrogen. In some embodiments, a polyphosphate may be any phosphate ester having two or more phosphate moieties. In some embodiments, a polyphosphate may be any phosphate esters having three or more phosphate moieties.

Any of the polyphosphorolyzing agents described herein may be combined with any other polyphosphorolyzing agents. In some embodiments, the one or more polyphosphorolyzing agents may be pyrophosphate ($PP_i$) in combination with at least one or more other polyphosphorolyzing agents. Any of the one or more polyphosphorolyzing agents may be used in the form of a salt (e.g., sodium).

Typically, the APP reactions as described herein further include one or more biocatalysts (e.g., enzyme(s)) having polyphosphorolysis activity to generate one or more nucleoside triphosphates. An exemplary one or more biocatalyst that may be used in APP is a DNA polymerase that catalyzes polymerization of nucleoside triphosphates and polyphosphorolysis of duplexes of DNA in the presence of one or more polyphosphorolyzing agents as described herein. Exemplary DNA polymerases having polyphosphorolysis activity include but are not limited to thermostable Tfl, Taq, and/or genetically engineered DNA polymerases (e.g., AMPLITAQFS, THERMOSEQUENASE), those having the active site mutation F667Y or the equivalent of F667Y (e.g., in Tth) which shows improved affinity for dideoxynucleotide as incoming nucleotide (e.g., smaller $K_m$ for ddNTP)), RQ1 as described in U.S. Pat. No. 7,422,872 and mutants thereof (e.g., RQY in which 669 is substituted by tyrosine, which may provide for reverse transcription and/or direct sequencing of RNA), THERMINATOR I (NEB), THERMINATOR II, THERMINATOR III, and/or THERMINATOR GAMMA (all available from NEB), among others. These and other potentially suitable DNA polymerases may be described in, for example, U.S. Pub. 2008/0254525A1, U.S. Pub. 2007/0020622A1, U.S. Pub. 2007/0009924A1, U.S. Pat. Nos. 4,889,818, 4,965,188, 5,047,342, 5,079,352, 5,270,179, 5,374,553, 5,436,149, 5,512,462, 5,614,365, and/or 6,228,628B1. It has been found that the use of such genetically engineered DNA polymerases may improve the efficiency of APP.

In some embodiments using APP, the polyphosphorolyzing agents are used under conditions, in concentrations, and with biocatalysts and other reaction components described in U.S. Pat. No. 8,932,813, all of which disclosure is herein incorporated by reference.

In certain embodiments, the provided methods for detecting and/or quantitating miRNA comprise the step of target cDNA amplification using activation by polyphosphorolysis (APP) in the presence of at least one polyphosphorolyzing agent. In certain embodiments, the at least one polyphosphorolyzing agent is a diphosphate, a triphosphate, a tetraphosphate, a pentaphosphate or a hexaphosphate. In certain embodiments of the provided methods, the polyphosphorolyzing agent is triphosphate. In certain embodiments of the provided methods, the polyphosphorolyzing agent is hexaphosphate. In some embodiments, the one or more polyphosphorolyzing agents may be pyrophosphate ($PP_i$) in combination with at least one or more other polyphosphorolyzing agents.

In certain embodiments, methods for amplifying target nucleic acids use activation by pyrophosphorolysis-activated polymerization (PAP) reactions. PAP may be used to polymerize and/or amplify nucleic acid molecules, including but not limited to ribonucleic acid (e.g., RNA) and/or deoxyribonucleic acid (e.g., DNA), or hybrids thereof. PAP reactions and uses thereof in polymerization and amplification reactions is described, for example, in U.S. Pat. No. 7,033,763, herein incorporated by reference in its entirety. In PAP, the annealed activatable oligonucleotide P* is pyrophosphorolyzed with pyrophosphate and an enzyme that exhibits polyphosphorolyzing activity. This activates the oligonucleotide P* by removal of the hybridized non-extendible 3' terminus. Accordingly, in certain embodiments, amplification of the target miRNA cDNA uses PAP and pyrophosphate as the pyrophosphorolyzing agent.

In certain embodiments, for target cDNA amplification reactions using APP or PAP, a forward primer or a reverse primer comprises a non-extendible nucleotide at the 3' terminus. In certain embodiments, for target cDNA amplification reactions using APP or PAP, both a forward primer and a reverse primer comprises a non-extendible nucleotide at the 3' terminus.

A hybridization method may also be used to assay the ligation product. Non-limiting examples of suitable hybridization methods include nucleic acid microarray. Microarray analyses may be performed using commercially available equipment and following the manufacturer's protocols. Typically, single-stranded nucleic acids are attached (arrayed) to a microchip surface. The arrayed sequences are then hybridized (probed) with nucleic acids, which may be fluorescently labeled. After stringent washing to remove the non-specifically bound nucleic acids, the chip surface is generally scanned by confocal laser microscopy or by another detection method, such as CCD camera. Methods of analysis of the raw fluorescent data are known in the art. A variety of arrayed nucleic acid and probe combinations may be used to detect the ligation product of the present teachings.

The 5' ligation adaptor may be free in solution, such that the mature small RNA or cDNA thereof is detected in solution. Alternatively, the 5' ligation adaptor may be attached to a solid support, whereby the 3'-terminal end of the 5' ligation adaptor is free. Thus, in this embodiment, the mature small RNA is attached to the ligation adaptor that is attached to the solid support. In other embodiments, the universal RT primer comprising a poly(T) portion may be attached to a solid support, whereby the 3'-terminal end of the universal RT primer is free. Thus, in this embodiment, the cDNA of the small RNA extended from the universal primer is attached to the solid support. Non-limiting examples of a suitable solid support include a glass surface, a silica surface, a plastic surface, a polymer surface, a co-polymer surface or a metal surface.

As used herein, the term "next generation sequencing" or "NGS" generally refers to high throughput sequencing technologies, including, but not limited to, massively parallel signature sequencing, high throughput sequencing, sequencing by ligation (e.g., SOLiD sequencing), proton ion semiconductor sequencing, DNA nanoball sequencing, single molecule sequencing, and nanopore sequencing. In certain embodiments, the ligation adaptor and/or universal RT primer contain nucleotide sequences which are compatible with a particular NGS chemistry or workflow. In certain embodiments, use of a ligation adaptor and/or universal RT primer having sequences which are complementary to sequences used in particular NGS reactions allows the cDNA of the polyadenylated, adaptor-ligated mature small RNA or the amplified product thereof to undergo NGS profiling and sequencing.

As used herein, the term "reaction vessel" generally refers to any container in which a reaction can occur in accordance with the present teachings. In some embodiments, a reaction vessel may be a microcentrifuge tube and other containers of the sort in common practice in modern molecular biology laboratories. In some embodiments, a reaction vessel may be a well in a microtiter plate (e.g., 96-well plate, 384-well plate), a spot on a glass slide, a well in an Applied Biosystems™ TaqMan™ Array Card (Thermo Fisher Scientific, Inc.) or a through-hole of a Applied Biosystems™ TaqMan™ OpenArray™ plate (Thermo Fisher Scientific, Inc.). For example, a plurality of reaction vessels may reside on the same support. In some embodiments, lab-on-a-chip-like devices, available for example from Caliper and Fluidigm, can provide for reaction vessels. In some embodiments, various microfluidic approaches may be employed. It will be recognized that a variety of reaction vessels are available in the art and fall within the scope of the present teachings.

As described, provided herein is a universal 5' ligation adaptor comprising a universal forward primer portion located at the 5' terminal region. Also provided is a universal RT primer comprising a poly(T) portion and a tail portion, the tail portion comprising a universal reverse primer portion. In certain embodiments, compositions are provided that comprise the universal 5' ligation adaptor. In certain embodiments, compositions are provided that comprise both the universal 5' ligation adaptor and the universal RT primer. In certain embodiments, compositions are provided that further comprise a universal forward and reverse primer pair, the primer pair being specific for the forward primer portion of the 5' adaptor and for the reverse primer portion of the RT primer. In certain embodiments, compositions are provided that further comprise a blocking oligonucleotide. In certain embodiments, such compositions are reaction compositions.

In certain embodiments, the present teachings also provide kits designed to expedite performing certain methods. In some embodiments, kits serve to expedite the performance of the methods of interest by assembling two or more components used in carrying out the methods. In some embodiments, kits may contain components in pre-measured unit amounts to minimize the need for measurements by end-users. In some embodiments, kits may include instructions for performing one or more methods of the present teachings. In certain embodiments, the kit components are optimized to operate in conjunction with one another.

In certain embodiments, the present teachings provide a kit comprising a 5' ligation adaptor, and a universal RT primer comprising an poly(T) portion. In certain embodiments, the kits may further comprise one or more of a ligase, a reverse transcriptase, and a DNA polymerase. In some embodiments, the kits may comprise a universal primer pair, the primer pair being specific for the forward primer portion of the 5' adaptor and for the reverse primer portion of the RT primer. In some embodiments, the kits may further comprise primer pairs specific for one or more mature small RNA. In some embodiments, the kits may comprise a plurality of primer pairs, wherein each primer pair is in one reaction vessel of a plurality of reaction vessels. In some embodiments, the kits may comprise a detector probe. In some embodiments, the detector probe comprises a nucleotide of the 5' adaptor or the universal RT primer in the amplification product or a nucleotide of the 5' adaptor or the universal RT primer complement in the amplification product and the detector probe further comprises a nucleotide of the 3' end region of the mature small RNA or a nucleotide of the 5' end region of the mature small RNA in the amplification product or a nucleotide of the 3' end region of the mature small RNA or a nucleotide of the 5' end region of the mature small RNA complement in the amplification product. In certain embodiments, the kit may further comprise a blocking oligonucleotide.

The methods provided herein are of use in detecting or quantitating mature small RNA in a sample. In some embodiments, the methods provided may be used to detect and/or distinguish a specific species of mature small RNA from among other species of small RNAs in the sample. In some embodiments, the methods provided may be used to distinguish several miRNAs from one another in a sample essentially concurrently in a single assay. In certain embodiments, the methods provided can detect very low quantities of mature small RNA in a sample. For example, in certain embodiments, the provided methods can detect fewer than about 1500 copies of an miRNA in a sample. In certain embodiments, the provided methods can detect fewer than about 1000 copies, fewer than about 800 copies, fewer than about 600 copies, fewer than about 400 copies, fewer than about 300 copies, fewer than about 200 copies, fewer than about 100 copies, fewer than about 60 copies, fewer than about 30 copies of an miRNA in a sample. In certain embodiments, the provided methods can detect as few as about 20 copies to about 1500 copies of an miRNA in a sample. Additional sensitivity ranges of certain embodiments of the provided methods include, but are not limited to, detection of about 20 copies to about 1000 copies, about 20 copies to about 600 copies, about 20 copies to about 300 copies, about 20 copies to about 100 copies, and about 20 copies to about 60 copies of an miRNA in a sample. In certain embodiments, the provided methods can detect as few as: about 1000 copies to about 1500 copies, about 500 copies to about 1000 copies, about 50 copies to about 500 copies, about 50 copies to about 200 copies, or about 50 copies to about 100 copies of an miRNA in a sample. In certain embodiments, the provided methods can detect as few as about 600 copies of an miRNA in a sample. In certain embodiments, the provided methods can detect as few as about 60 copies of an miRNA in a sample.

In certain embodiments, the provided methods can detect less than about 0.01 pM of an miRNA in a sample. In certain embodiments, the provided methods can detect less than about 0.001 pM of an miRNA in a sample. In certain embodiments, the provided methods can detect less than about 0.0001 pM of an miRNA in a sample. In certain embodiments, the provided methods can detect in the range of about 0.0001 pM to about 0.01 pM miRNA in a sample. In certain embodiments, the provided methods can detect in the range of about 0.0001 pM to about 0.001 pM miRNA in a sample. In certain embodiments, the provided methods can detect in the range of about 0.001 pM to about 0.01 pM miRNA in a sample. In certain embodiments, the provided methods can detect about 0.01 pM miRNA in a sample. In certain embodiments, the provided methods can detect in about 0.001 pM miRNA in a sample. In certain embodiments, the provided methods can detect about 0.0001 pM miRNA in a sample.

In some embodiments, the methods provided herein may be used in identifying and/or confirming mature small RNA biomarkers that may be used in disease detection and monitoring, treatment selection and monitoring, as well as patient diagnostic and/or prognostic methods. In methods for identifying and/or confirming mature small RNA biomarkers, RNA samples may be prepared from cells, tissue (frozen or fresh), formalin- or paraformalin fixed paraffin-embedded tissue (FFPE), urine, whole blood, blood plasma, blood serum, lymph, bone marrow, perspiration, saliva, and/or other biological secretions. Identifying biomarkers in readily accessible biological samples, for example blood, blood components, and urine, is highly desirable and small mature RNAs, like miRNAs, are known to circulate in the blood and are present in other bodily fluids. As demonstrated, the methods provided herein possess high sensitivity and specificity to detect and quantitate miRNA in RNA samples with relatively low copy number. The methods provided are also amenable to high sample throughput. The methods provided herein are of use in screening RNA samples from individuals or populations of varying states of health, age, or other conditions for the potential miRNA biomarkers.

The high sensitivity and specificity of the provided methods also are amenable to detecting and/or quantitating expression of small mature RNA and other RNA, such as mRNA or rRNA, in the same RNA sample. In some embodiments, for example, a portion of the RNA sample is used to detect and/or quantitate expression of small mature RNAs in the sample and another portion of the RNA sample is used to detect and/or quantitate expression of mRNA, allowing a correlation to be made between expression of the small mature RNA and the mRNA. This may be beneficial for small and/or limited RNA samples.

According to another embodiment of the present teachings, the methods disclosed herein may be used in diagnostic and/or prognostic methods for identifying diseases and/or in determining patient response to treatment with certain drugs, medications or methods of therapy. An exemplary condition that can be associated with mature small RNAs such as miRNA is cancer. Thus, the present teachings provide a method of diagnosing susceptibility to a cancer, prognosis of outcome for treatment of cancer, or the stage and/or identity of the cancer based on the miRNA profile of the sample.

Certain embodiments provide for the use of any of the methods disclosed herein for the diagnosis and/or prognosis of diseases, for example, cancer, including but not limited to breast cancer, prostate cancer, lung cancer, skin cancer, cancers of the reproductive tract, brain cancer, liver cancer, pancreatic cancer, stomach cancer, blood cancers (e.g., leukemia and lymphoma), sarcomas, melanomas, and the like; cardiovascular diseases; autoimmune diseases and disorders; and metabolic diseases and disorders. Another embodiment provides for the use of any of the methods disclosed herein in the diagnosis or determination of responsiveness to drugs and medical treatment.

While the present teachings have been described in terms of these exemplary embodiments, the skilled artisan will readily understand that numerous variations and modifications of these exemplary embodiments are possible without undue experimentation. All such variations and modifications are within the scope of the current teachings. Aspects of the present teachings may be further understood in light of the following examples, which should not be construed as limiting the scope of the teachings in any way.

EXAMPLES

Example 1: miRNA Analysis Using Two-Ended Universal Tailing RT-qPCR

Total RNAs from human brain were obtained from Ambion™ (Thermo Fisher Scientific, Inc.). Synthetic miRNA oligonucleotides were purchased from Integrated DNA Technologies (IDT, Coralville, Iowa). Ligation adaptor, reverse transcription and pre-amplification primers, and TaqMan™ assays were obtained from Applied Biosystems™ (Thermo Fisher Scientific, Inc.).

Step 1: Poly(A) Tailing

The poly A tailing of synthetic miRNAs or total RNA was performed by combining the following components:

0.5 µl 10X Poly(A) Pol Reaction Buffer
0.5 µl 10 mM ATP
0.025 µl 40 U/µl RNase Inhibitor
0.3 µl 5 U/µl Poly(A) Polymerase
2 µl Synthetic miRNAs (ranging from 60 to 6 × 10$^7$ copies) or Total RNA (ranging from 1 to 25 ng)
1.675 µl Nuclease-Free Water 5 µl Total Poly(A) Reaction Volume The poly(A) reaction was mixed, spun briefly, and incubated in a thermal cycler at 37° C. for 45 minutes, 65° C. for 10 minutes, 4° C. hold.

Step 2: Ligation Reaction

The ligation reaction was performed to ligate a 5' RNA adaptor to the polyA tailed RNA having a 5'-terminal monophosphate (including polyA-tailed miRNA). The ligation reaction was performed by combining the following components:

3 µl 5X T4 DNA Ligase Buffer
4.5 µl 50% PEG8000
0.15 µl 50 µM Ligation Adaptor
0.075 µl 40 U/µl RNase Inhibitor
1.5 µl 10 U/µl RNA Ligase I
0.775 µl Nuclease-Free Water 10 µl Total Volume Above components were mixed and then added to the 5 µl poly (A) reaction from Step 1 above for a total ligation reaction volume of 15 µl. The ligation reaction was mixed, spun briefly, and incubated in a thermal cycler at 16° C. for 60 minutes, 4° C. hold.

Step 3: Reverse Transcription Reaction

The reverse transcription (RT) step synthesizes the first strand cDNA from the ligation product from step 2 and incorporates the universal RT primer into the product. The RT reaction was performed by combining the following components:

6 ul 5X RT Buffer
1.2 ul 100 mM dNTP Mix (25 mM each)
1.5 ul 5 uM Universal RT primer
3 ul 10X SuperScript™ Enzyme Mix
3.3 ul Nuclease-free Water 15 ul Total Volume Above components were mixed and then added to the 15 ul ligation reaction from step 2 for a total RT reaction volume of 30 ul. The RT reaction was mixed, spun briefly, and incubated in a thermal cycler at 42° C. for 15 minutes, 85° C. for 5 minutes, 4° C. hold.

Step 4: Pre-Amplification Reaction (Optional)

Pre-amplification (pre-amp) is an optional step to increase detection sensitivity. The pre-amp reaction was performed by combining the following components:

5 ul cDNA from RT reaction (from step 3)
25 ul 2X TaqMan™ PreAmp Master Mix
0.25 ul 50 uM Pre-amp Forward and Reverse Universal Primers
19.75 ul Nuclease-free Water 50 ul Total Pre-amp Reaction Volume The pre-amp reaction was mixed, spun briefly, and incubated in a thermal cycler at 95° C. for 10 minutes, followed by 12 cycles of (95° C. for 15 seconds, 60° C. for 2 minutes), then 99° C. for 10 minutes and 4° C. hold.

Step 5: Real-Time Polymerase Chain Reaction (qPCR)

Real-time PCR was performed for the detection of the miRNA. The RT or pre-amp reaction was diluted 1:10 in 0.1×TE buffer. qPCR was prepared by combining the following components:

10 ul 2X TaqMan™ Fast Advanced Master Mix
1 ul 20X TaqMan™ Assay
4 ul Nuclease-free Water
5 ul diluted RT or pre-amp reaction 20 ul Total PCR Reaction Volume PCR was mixed and spun briefly. The reactions were run with real-time PCR system such as the ViiA™7 Real-Time PCR System or the ABI PRISM™ 7900HT Sequence Detection System. Data was analyzed according to the instrument specifications and guidelines.

Figure 2A:
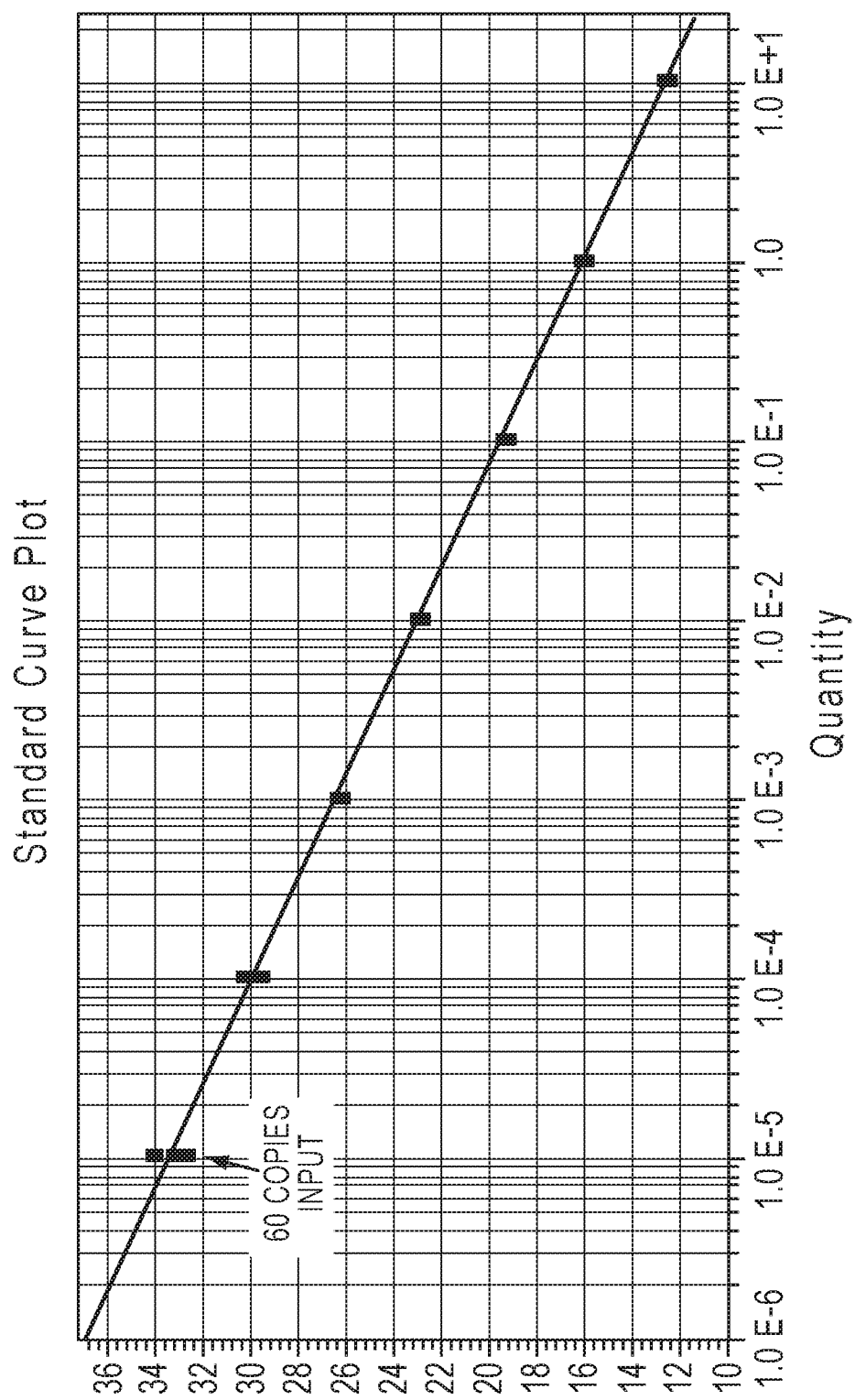
FIGS. 2A and 2B graphically represent the linear dynamic range (FIG. 2A) and sensitivity (FIG. 2B) of the methods according to the embodiments of the present teachings.
Figure 2B:
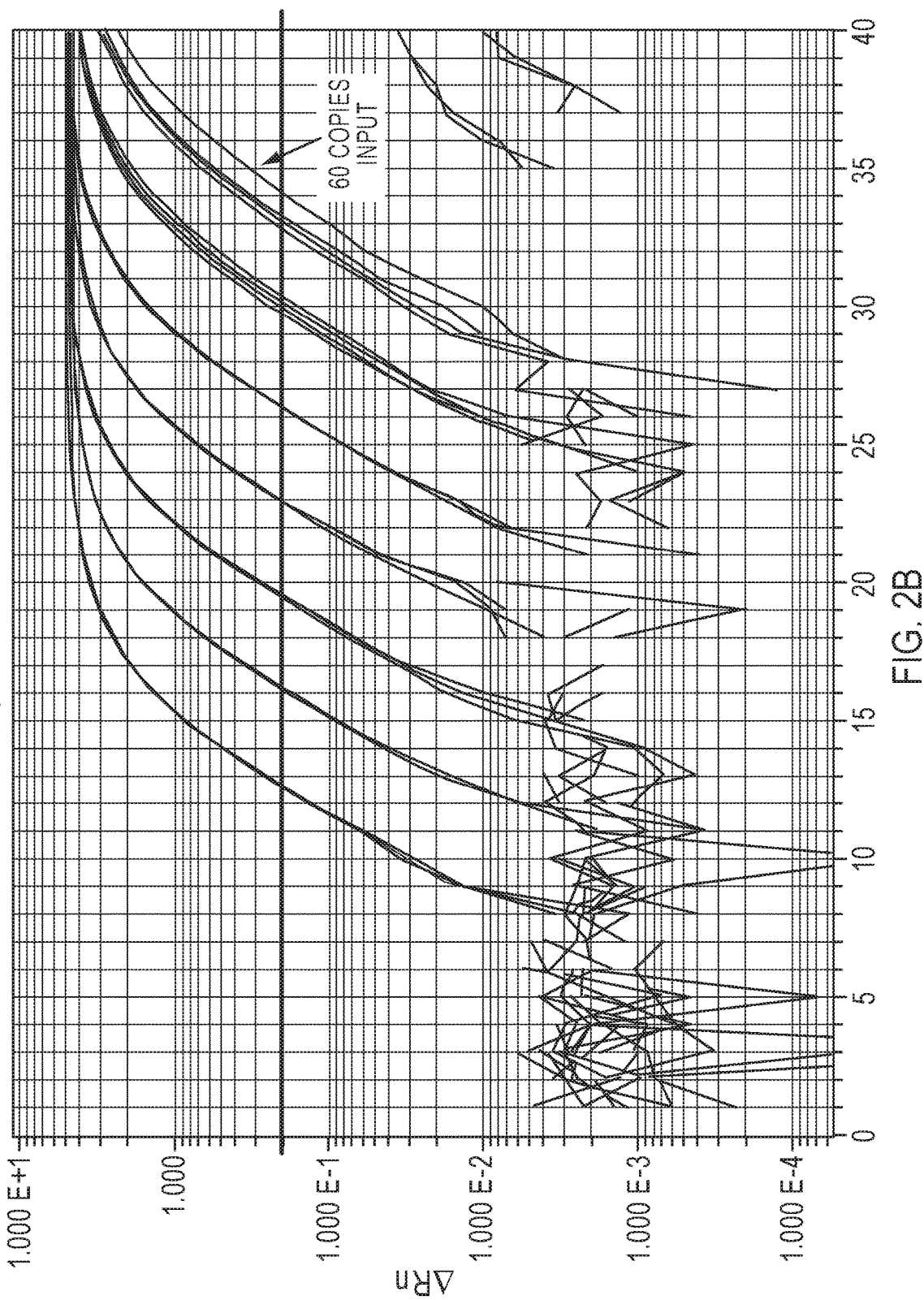
Figure 3:
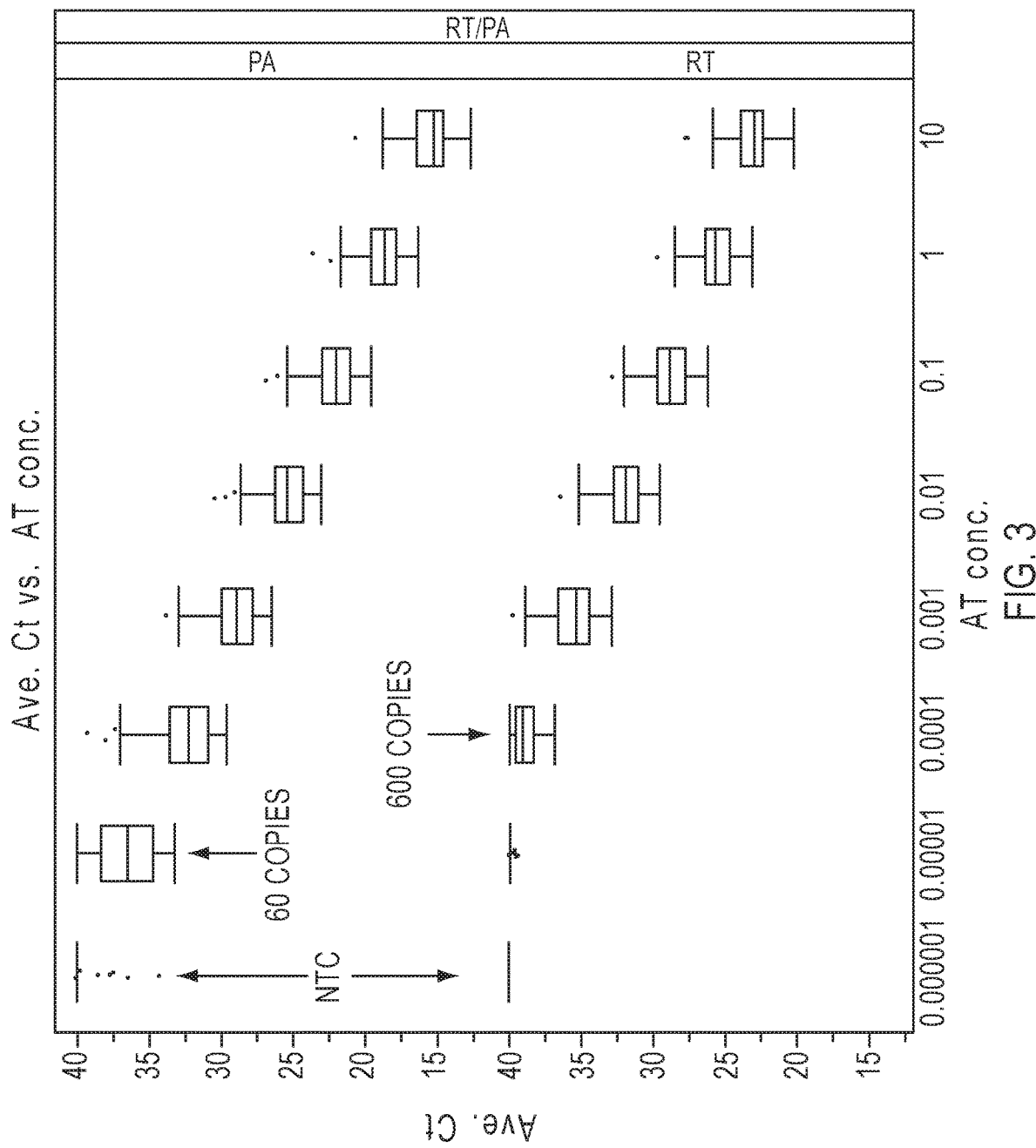
FIG. 3 graphically depicts a comparison of average sensitivity for 48 miRNA assays with pre-amplification (PA) and without pre-amplification (RT) across a range of input RNA amounts. NTC is no template control.

Using the workflow outlined above, two-ended universal tailing RT-qPCR assays were designed and performed to detect 48 miRNA species. The workflow was performed with and without a pre-amplification step. A very good linear response to synthetic template titration was obtained with a 6-log linear dynamic range with input copies from 60 to 60 million and a limit of detection of 60 copies with pre-amplification (FIGS. 2A and 2B). FIG. 3 depicts a comparison of the average cycle threshold ("Ct") to input RNA amount ("AT conc.") for all 48 miRNA assays without pre-amplification ("RT") and with pre-amplification ("PA"). As shown in FIG. 3, tight Ct distribution across the 48 assays is obtained with uniform results across the entire workflow and little ligation bias.

Example 2: Comparison of miRNA Detection Assays miRNA detection data using the assays and methods described herein were compared to the market gold standard TaqMan™ Individual MicroRNA Assays. The two-ended universal tailing assay described herein were performed as described in Example 1, either without or with a 12 cycle preamplification step. The TaqMan™ Individual MicroRNA Assays was performed according to the product specifications and guidelines.

Total RNA from normal human brain was used to detect the expression level of 4 high, 4 medium, and 3 low expressing miRNAs. Dilution factor was taken into account so that the input amount and copy number in PCR were the same between the universal tailing assay described herein and TaqMan™ Individual MicroRNA Assays. Assays were performed with an input amount of 25 ng of total RNA and with 2.5 ng total RNA, along with no template control (NTC).

Figure 4:
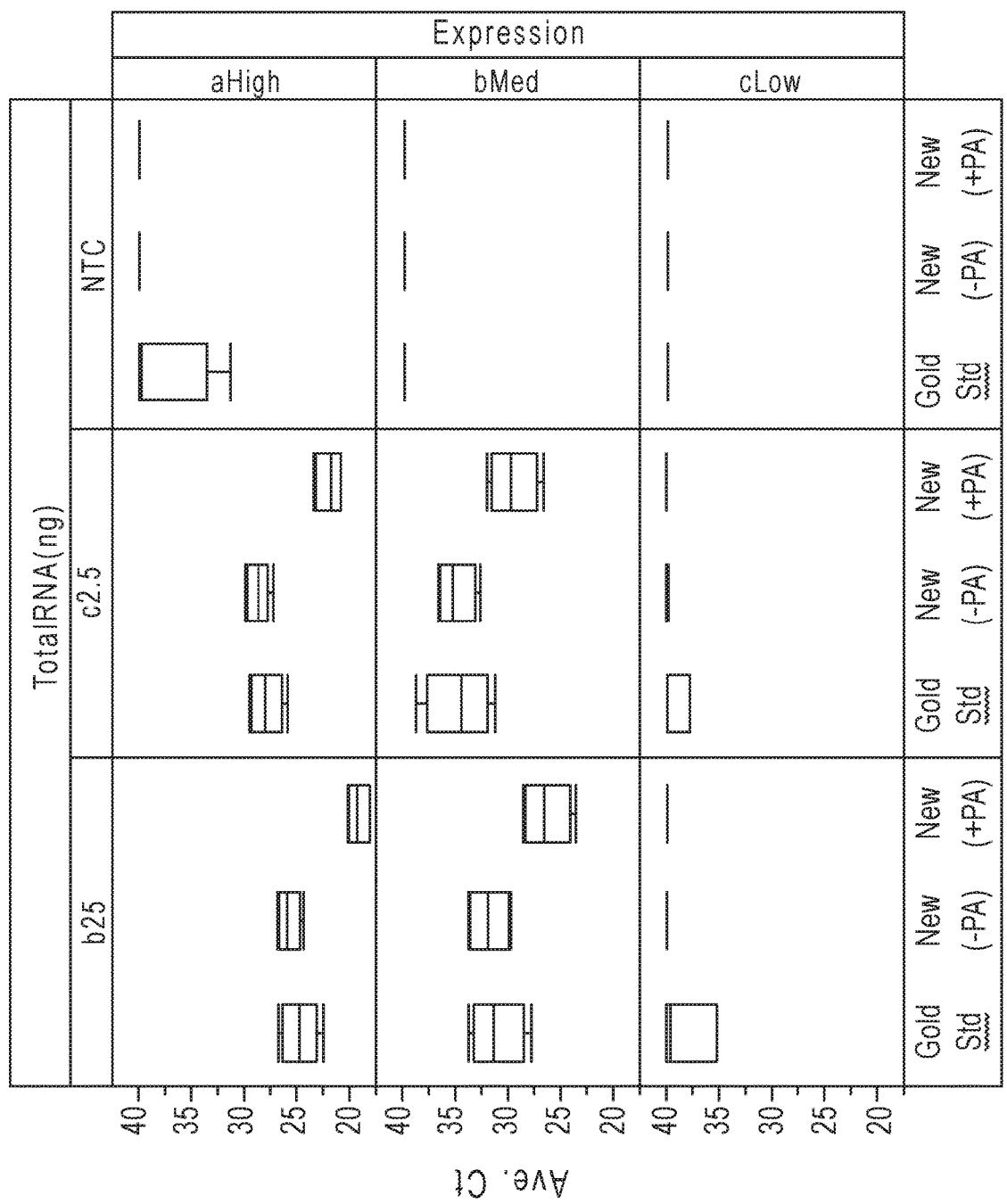
FIG. 4 graphically depicts a sensitivity comparison of assay methods in the detection of miRNA in a preparation of total RNA from brain. Detection methods: TaqMan™ Individual MicroRNA Assays (Gold Std); two-ended universal tailing miRNA assays according to embodiments of the present teachings with (+PA) and without (−PA) a pre-amplification step.

As can be seen in FIG. 4, without a pre-amplification step ("−PA"), the assay provided herein is at least as sensitive as the market gold standard assay in miRNA detection ("Gold Std"). Inclusion of a pre-amplification step in the provided assay resulted in a significant increase in detection sensitivity (FIG. 4 "+PA").

Example 3: miRNA Analysis of Total RNA from Tissue Samples

Total RNAs from human tissue (brain, kidney, colon, heart, liver, and lung) were obtained from Ambion™ (Thermo Fisher Scientific, Inc.). Reaction components are from the TaqMan™ Advanced miRNA cDNA Synthesis kit and TaqMan™ Advanced miRNA Assays obtained from Applied Biosystems™ (Thermo Fisher Scientific, Inc.).

Step 1: Poly(A) Tailing
The poly A tailing of total RNA was performed by combining the following components:

| |
|---|
| 0.5 µl 10X Poly(A) Pol Reaction Buffer |
| 0.5 µl 10 mM ATP |
| 0.3 µl 5 U/µl Poly(A) Polymerase |
| 2 µl Total RNA (eg, ranging from 1 to 25 ng) |
| 1.7 µl Nuclease-Free Water |
| 5 µl Total Poly(A) Reaction Volume |

The poly(A) reaction was mixed, spun briefly, and incubated in a thermal cycler at 37° C. for 45 minutes, 65° C. for 10 minutes, 4° C. hold.

Step 2: Ligation Reaction
The ligation reaction was performed to ligate a 5' RNA adaptor to the polyA tailed RNA having a 5'-terminal monophosphate (including polyA-tailed miRNA). The ligation reaction was performed by combining the following components:

| |
|---|
| 3 µl 15X Ligase Buffer |
| 4.5 µl 50% PEG8000 |
| 0.6 µl 25X Ligation Adaptor |
| 1.5 µl 10 U/µl RNA Ligase I |
| 0.4 µl Nuclease-Free Water |
| 10 µl Total Volume |

Above components were mixed and then added to the 5 µl poly (A) reaction from Step 1 above for a total ligation reaction volume of 15 µl. The ligation reaction was mixed, spun briefly, and incubated in a thermal cycler at 16° C. for 60 minutes, 4° C. hold.

Step 3: Reverse Transcription Reaction
The reverse transcription (RT) step synthesizes the first strand cDNA from the ligation product from step 2 and incorporates the universal RT primer into the product. The RT reaction was performed by combining the following components:

| |
|---|
| 6 ul 5X RT Buffer |
| 1.2 ul 100 mM dNTP Mix (25 mM each) |
| 1.5 ul 5 uM Universal RT primer |
| 3 ul 10X RT Enzyme Mix |
| 3.3 ul Nuclease-free Water |
| 15 ul Total Volume |

Above components were mixed and then added to the 15 ul ligation reaction from step 2 for a total RT reaction volume of 30 ul. The RT reaction was mixed, spun briefly, and incubated in a thermal cycler at 42° C. for 15 minutes, 85° C. for 5 minutes, 4° C. hold.

Step 4: Pre-Amplification Reaction (Optional)
The optional pre-amplification (pre-amp) reaction was performed by combining the following components:

| |
|---|
| 5 ul cDNA from RT reaction (from step 3) |
| 25 ul 2X miR-Amp Master Mix |
| 2.5 ul 20X miR-Amp primer mix (Forward and Reverse Universal Primers) |
| 17.5 ul Nuclease-free Water |
| 50 ul Total Volume |

The pre-amp reaction was mixed, spun briefly, and incubated in a thermal cycler at 95° C. for 10 minutes, followed by 14 cycles of (95° C. for 3 seconds, 60° C. for 30 seconds), then 99° C. for 10 minutes and 4° C. hold.

Step 5: Real-Time Polymerase Chain Reaction (qPCR)
Real-time PCR with fast cycling was performed for the detection of the miRNA. The RT or pre-amp reaction was diluted 1:10 in 0.1×TE buffer. qPCR was prepared by combining the following components:

| |
|---|
| 5 ul 2X TaqMan ™ Fast Advanced Master Mix |
| 0.5 ul 20X TaqMan ™ Advanced miRNA Assay |

| |
|---|
| 2 ul Nuclease-free Water |
| 2.5 ul diluted RT or pre-amp reaction |
| 20 ul Total PCR Reaction Volume |

PCR was mixed and spun briefly. The reactions were run with real-time PCR system such as the ViiA™7 Real-Time PCR System or the QuantStudio real-time PCR systems. The reactions were incubated in the real-time PCR instrument at 95° C. for 20 seconds, followed by 40 cycles of (95° C. for 1 second, 60° C. for 20 seconds), then 4° C. hold. Data was analyzed according to the instrument specifications and guidelines.

Figure 5A:
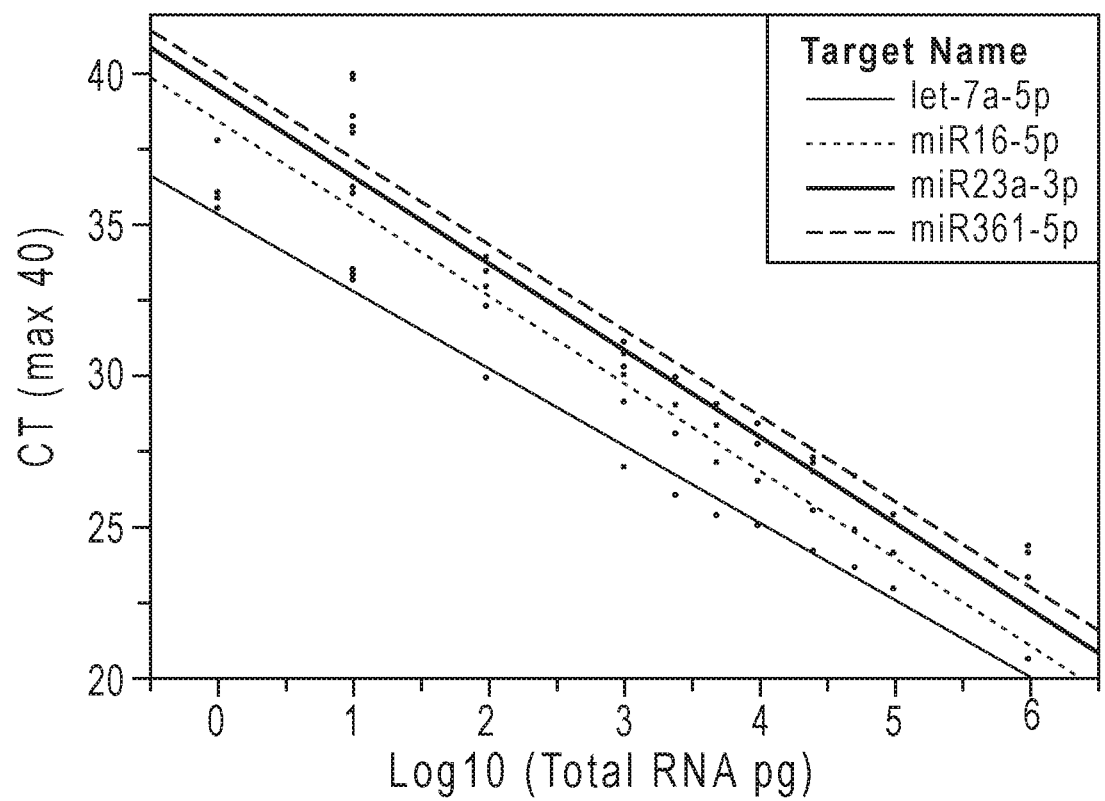
FIGS. 5A-5D graphically represent the linear dynamic range and sensitivity of methods according to embodiments of the present teachings in assessing 4 miRNAs in total RNA from brain tissue (FIGS. 5A and 5B) and from kidney tissue (FIGS. 5C and 5D).
Figure 5B:
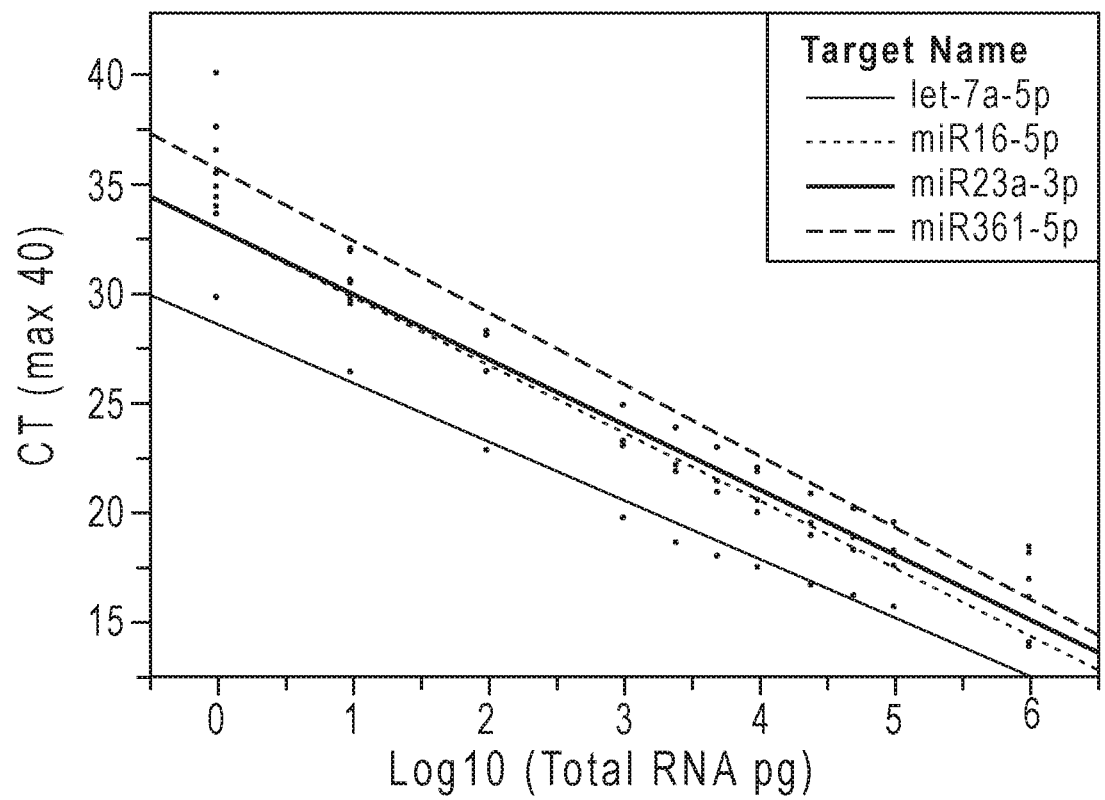
Figure 5C:
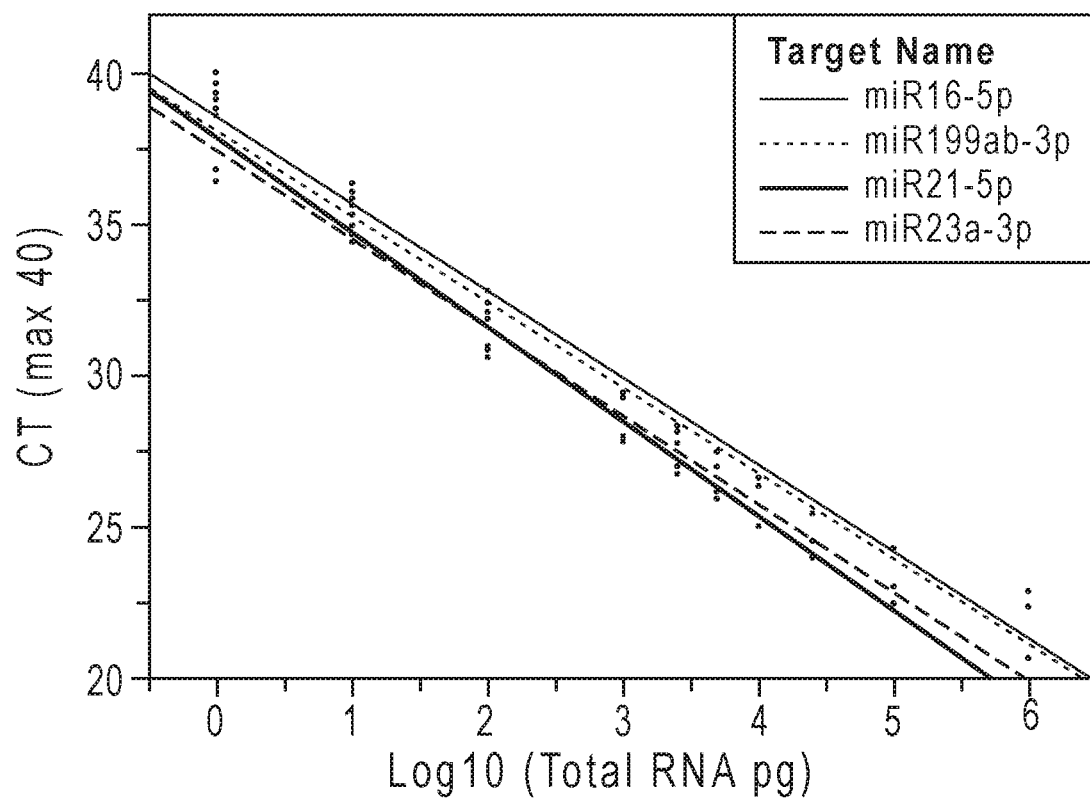
Figure 5D:
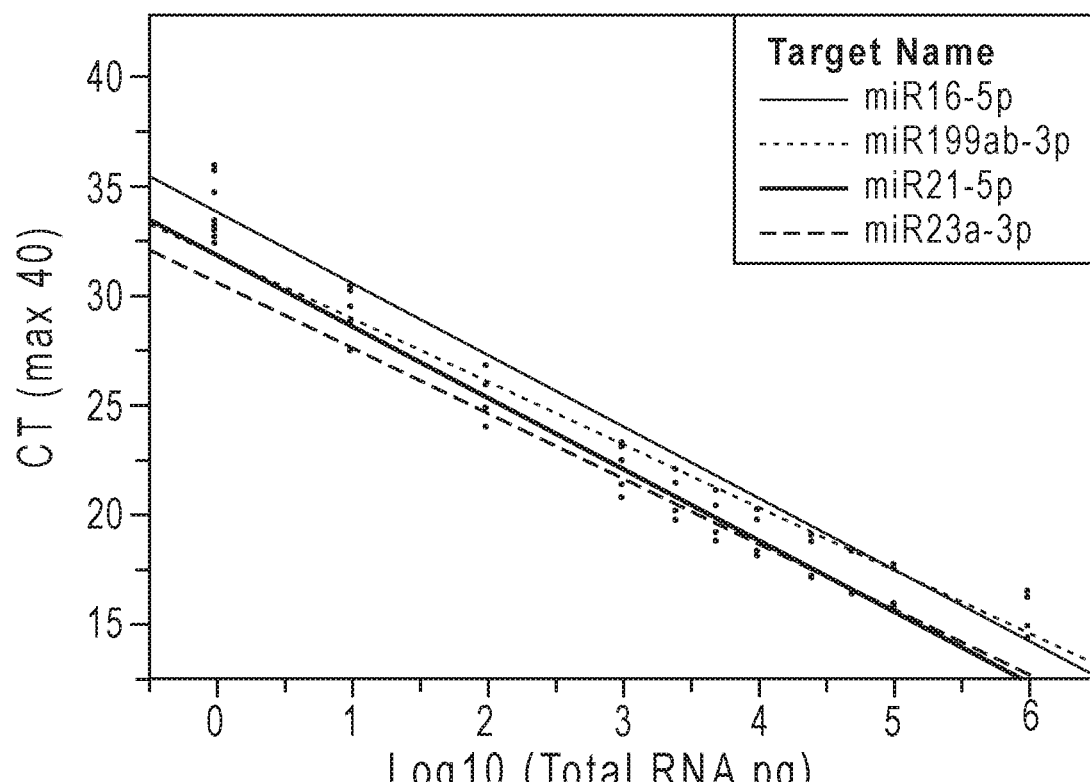

The assays were designed and performed to detect a variety of miRNA species from the various tissues. A five-log range of total RNA (1 pg to 1 ug) from brain and kidney tissue was used in the workflow and each assayed for 4 miRNAs. The results depicted in FIGS. 5A-5D show good linear responses to the RNA input across the 5 log range for all 4 miRNAs. miRNAs let-7a-5p, miR16-5p, miR23a-3p, and miR361-5p were measured in brain total RNA (FIGS. 5A-5B) and miRNAs miR16-5p, miR199ab-3p, miR21a-5p, and miR23-3p were measured in kidney total RNA (FIGS. 5C-5D). The miRNA detection assays were performed for cDNA preparations without pre-amplification (FIGS. 5A and 5C) and for preparations having undergone pre-amplification (FIGS. 5B and 5D). Inclusion of a pre-amplification step resulted in significant increases in detection sensitivity.

Figure 6A:
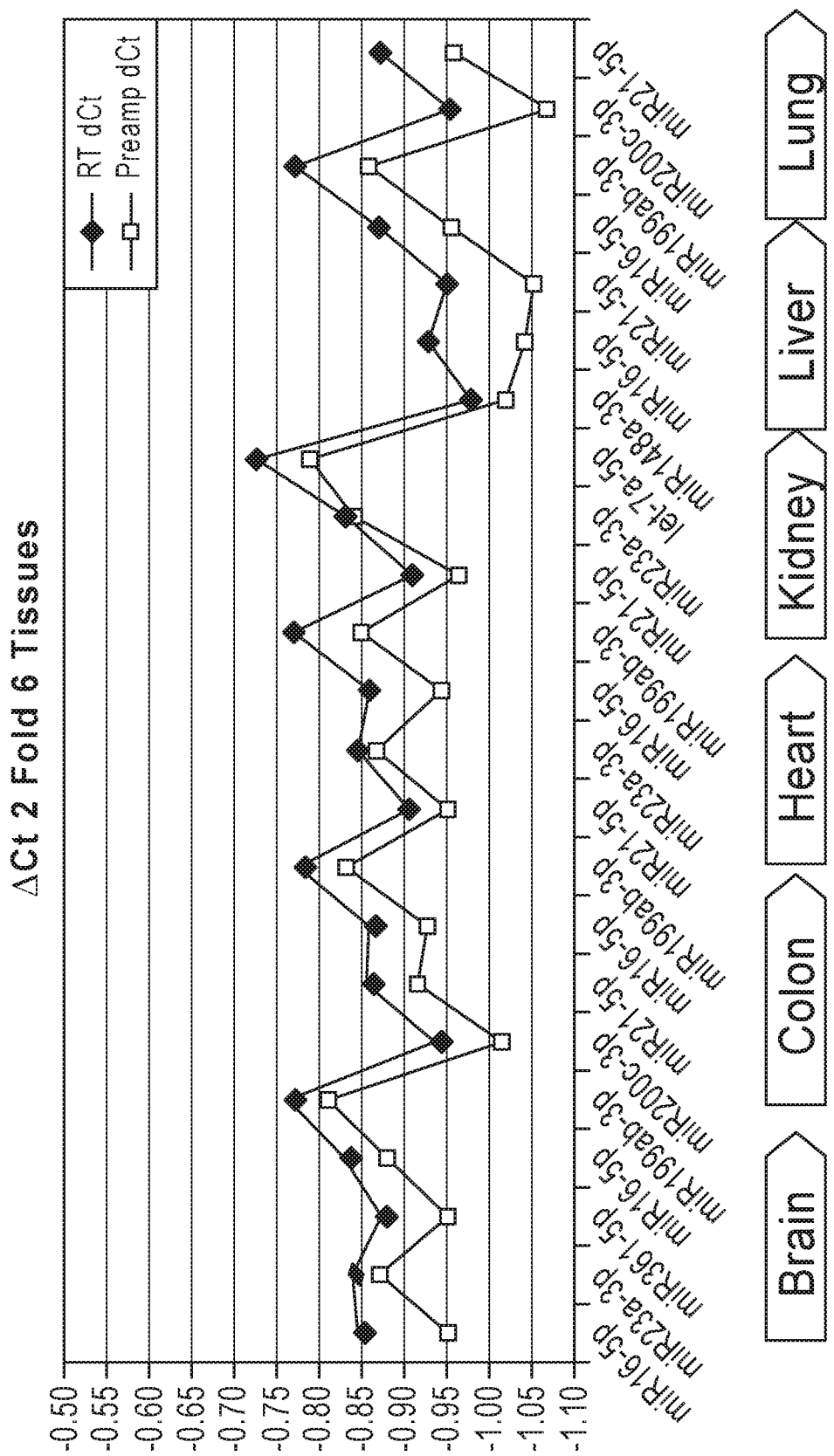
FIGS. 6A and 6B graphically represent 2 fold delta Ct (FIG. 6A) and discrimination (FIG. 6B) of miRNAs from 6 tissues measured according to the embodiments of the present teachings.
Figure 6B:
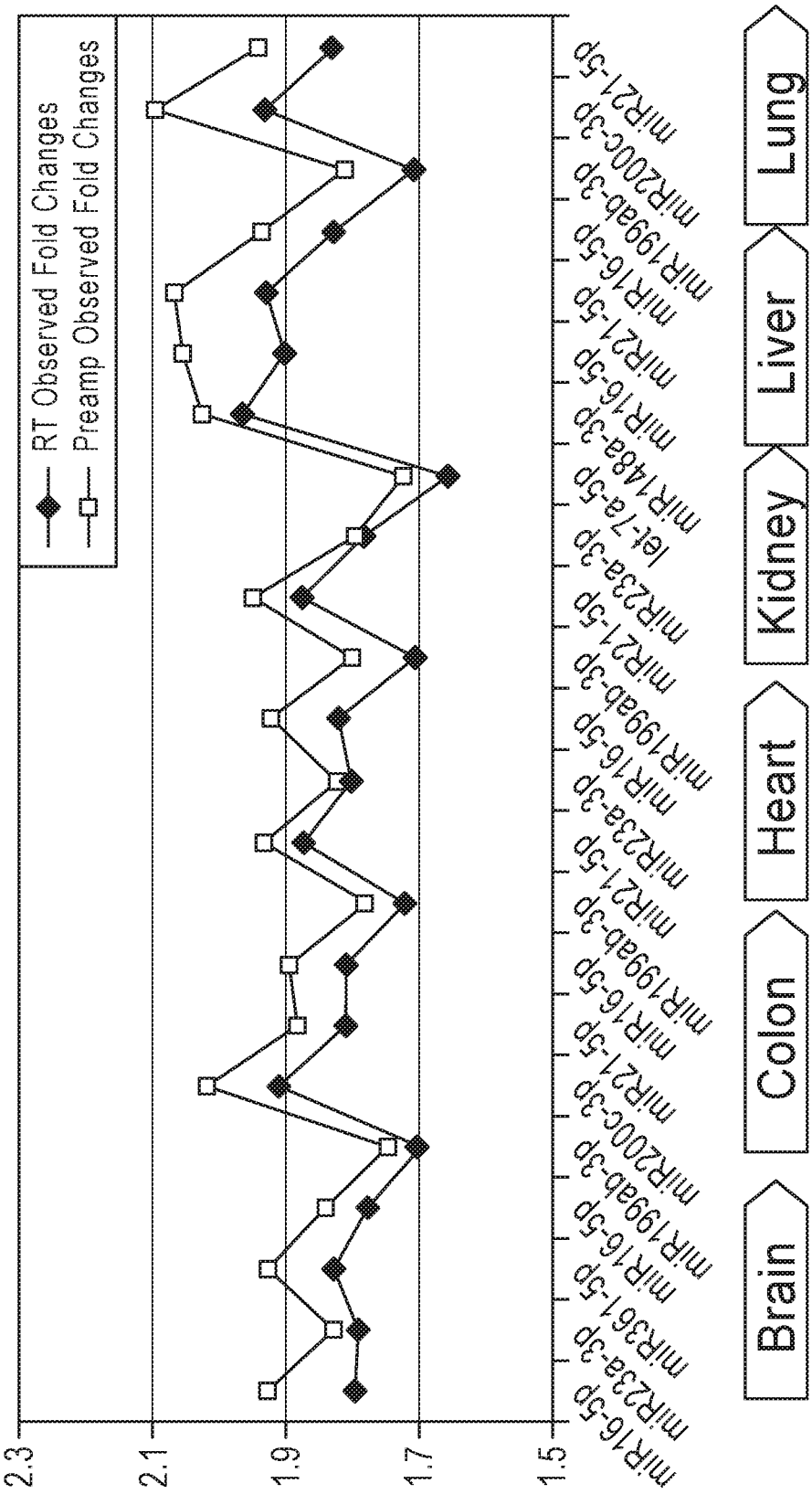

Total RNA from six tissues human tissue (brain, kidney, colon, heart, liver, and lung) were subjected to the RNA tailing workflow and miRNA detection assays described above. The cDNA and pre-amplified reaction products were subjected to 2-fold ΔCt and 2-fold dilution discrimination analysis (FIGS. 6A and 6B; diamond=without pre-amplification (RT); square=with pre-amplification). The results shown in FIG. 6B show the workflow meets 2-fold discrimination detection for gene expression studies.

Example 4: miRNA Analysis of Total RNA from Blood and Urine Samples

Total RNA (including miRNA) was prepared from samples of human blood serum (100 microliter), blood plasma (100 microliter), and urine (250 microliter) from healthy donors using two different procedures. In a high throughput procedure, total RNA was isolated from the samples (in duplicate) using MagMAX™ mirVana™ Total RNA Isolation kit (Ambion™, Thermo Fisher Scientific, Inc.) and serum specific protocol with the Thermo Scientific™ KingFisher™ FLEX instrument (96-well deep well head) according to manufacturers' instructions. In the other procedure, total RNA was isolated from the sample using the mirVana™ PARIS™ RNA purification kit (Ambion™, Thermo Fisher Scientific, Inc.) according to manufacturer's instructions.

A TaqMan™ Advanced cDNA Synthesis kit was used to produce universal tailed miRNA cDNA from two microliters of isolated total RNA and amplify the cDNA with miR-Amp pre-amplification in the procedure performed as described in Example 3. Following pre-amplification, TaqMan™ Advanced miRNA Assays and TaqMan™ Fast Advanced Master Mix was used in qPCR amplification reactions for miRNA detection and quantification, as described in Example 3. The pre-amplified cDNA was subjected to miRNA assays to detect 5 miRNA species: let7c, miR16, miR221, miR21, and miR26a.

Figure 7A:
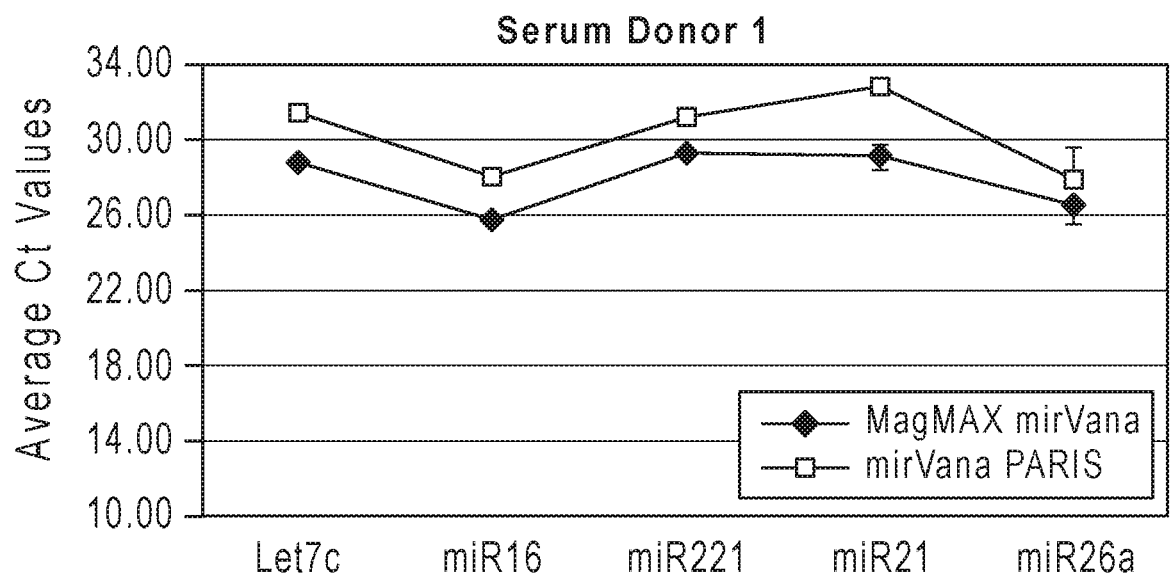
FIGS. 7A-7B graphically represent quantification of 5 miRNAs in RNA isolated from blood serum of two donors. miRNA levels were measured according to the embodiments of the present teachings.
Figure 7B:
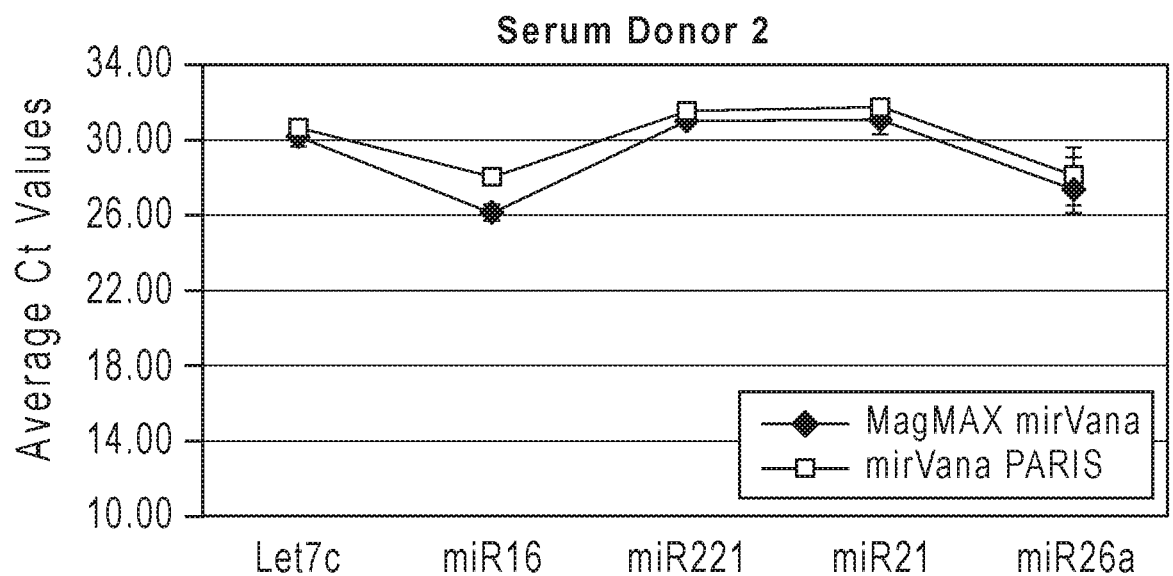
Figure 8A:
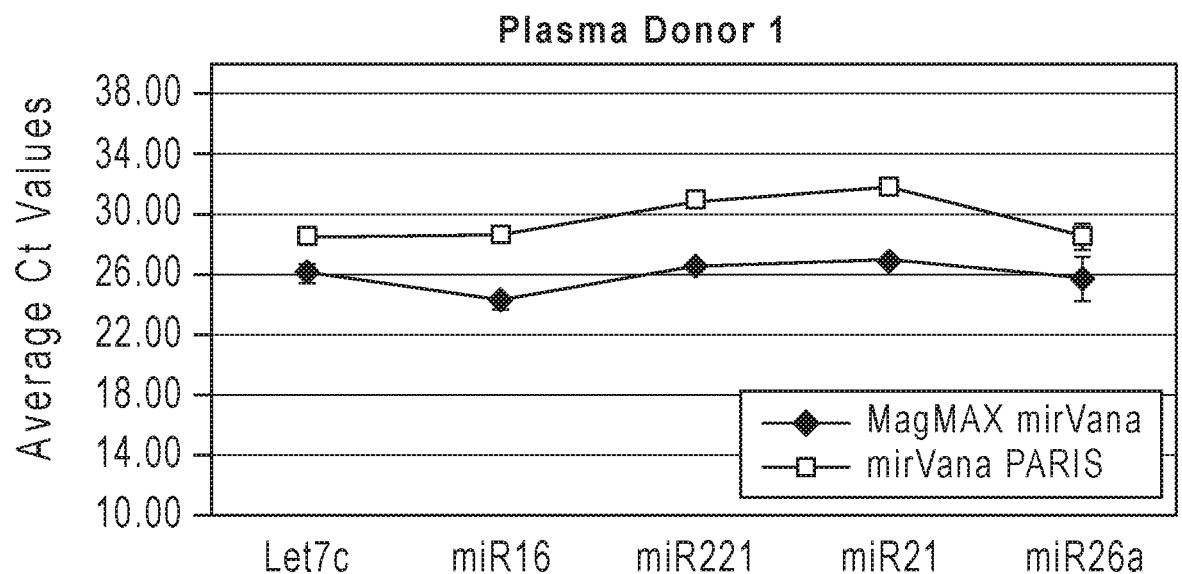
FIGS. 8A-8B graphically represent quantification of 5 miRNAs in RNA isolated from blood plasma of two donors. miRNA levels were measured according to the embodiments of the present teachings.
Figure 8B:
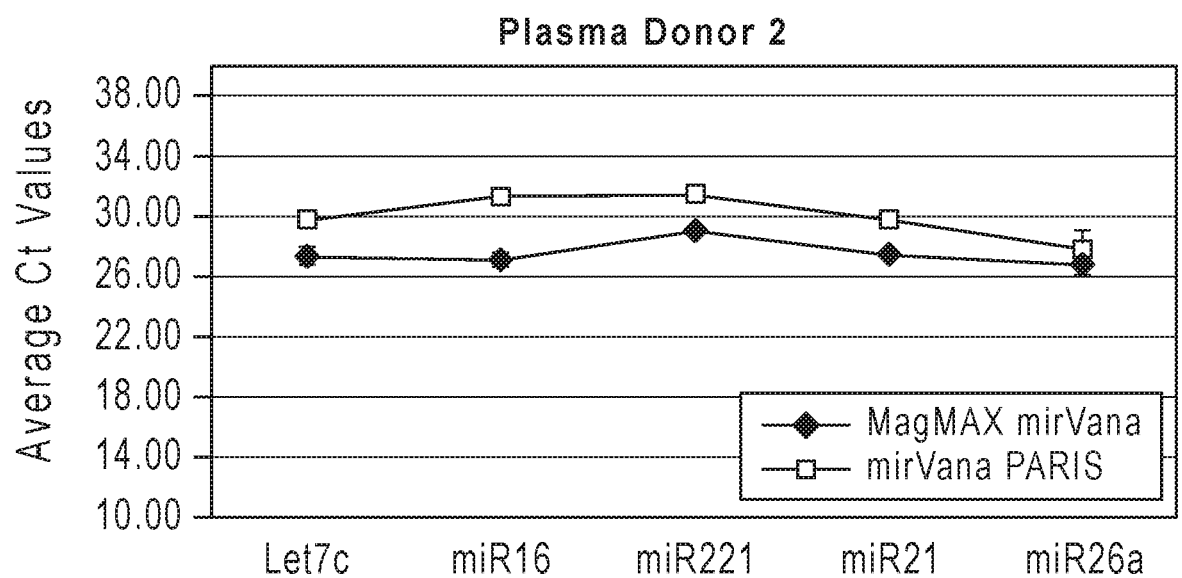
Figure 9A:
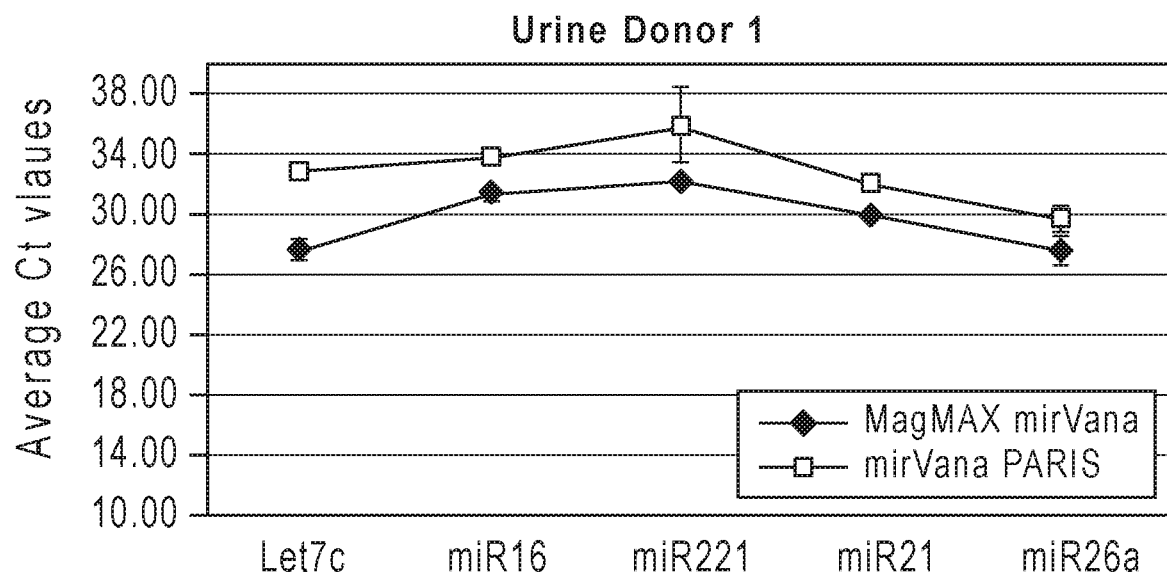
FIGS. 9A-9B graphically represent quantification of 5 miRNAs in RNA isolated from urine of two donors. miRNA levels were measured according to the embodiments of the present teachings.
Figure 9B:
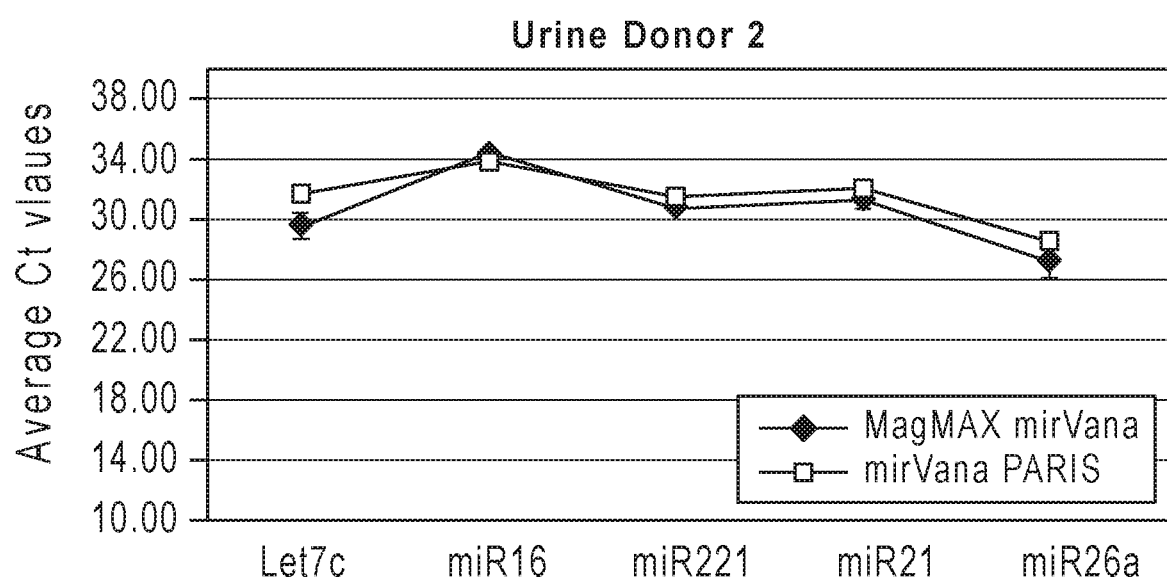

FIGS. 7A and 7B show the detection of the 5 miRNAs in RNA isolated from serum of two donors. FIGS. 8A and 8B show the detection of the 5 miRNAs in RNA isolated from plasma of two donors. FIGS. 9A and 9B show the detection of the 5 miRNAs in RNA isolated from urine of two donors. FIGS. 7A, 7B, 8A, 8B, 9A, and 9B show results from RNA isolated with the high throughput procedure (diamond, MagMAX™ mirVana™ kit), and RNA isolated with a gold standard (but not high throughput) RNA isolation procedure (square, mirVana™ PARIS™ kit).

What is claimed is:

1. A kit for synthesizing and amplifying a mature small RNA cDNA, the kit comprising:
    in solution, a single-stranded RNA adaptor comprising a 3' terminal —OH group and a universal forward primer portion;
    a reverse transcription (RT) primer, wherein the RT primer comprises a poly(T) portion and a tail portion and wherein the tail portion comprises a universal reverse primer portion;
    a single strand RNA ligase;
    a reverse transcriptase;
    a DNA polymerase; and
    a universal forward and reverse primer pair, wherein the universal forward primer can hybridize to the universal forward primer portion or its complement, and the universal reverse primer can hybridize to the universal reverse primer portion or its complement,
    wherein said kit does not comprise a splint oligonucleotide.

2. The kit of claim 1, further comprising one or more dNTPs, ATP, a buffer, and a salt of a divalent cation.

3. A composition for detecting a mature small RNA comprising, in solution:
    a cDNA of a mature small RNA, the cDNA comprising a reverse transcription (RT) primer sequence at the 5' end and an adaptor sequence at the 3' end, wherein the RT primer sequence comprises a poly(T) portion and a tail portion and wherein the tail portion comprises a universal reverse primer portion, and wherein the adaptor comprises a universal forward primer portion;
    poly(A) polymerase,
    RNA Ligase I,
    and a reverse transcriptase,
    wherein said composition does not comprise a splint oligonucleotide.

4. The composition of claim 3, further comprising a universal forward and reverse primer pair, wherein the universal forward primer can hybridize to the universal forward primer portion or its complement, and the universal reverse primer can hybridize to the universal reverse primer portion or its complement.

5. The composition of claim 4, further comprising a DNA polymerase.

* * * * *